(12) United States Patent
Kemp

(10) Patent No.: US 10,758,682 B2
(45) Date of Patent: Sep. 1, 2020

(54) AUTOINJECTOR

(71) Applicant: Sanofi-Aventis Deutschland GMBH, Frankfurt am Main (DE)

(72) Inventor: Thomas Kemp, Ashwell (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 122 days.

(21) Appl. No.: 16/163,388

(22) Filed: Oct. 17, 2018

(65) Prior Publication Data
US 2019/0105447 A1 Apr. 11, 2019

Related U.S. Application Data

(63) Continuation of application No. 14/903,351, filed as application No. PCT/EP2014/064425 on Jul. 7, 2014, now Pat. No. 10,137,255.

(30) Foreign Application Priority Data

Jul. 9, 2013 (EP) ...................................... 13175662

(51) Int. Cl.
*A61M 5/32* (2006.01)
*A61M 5/20* (2006.01)
*A61M 5/50* (2006.01)

(52) U.S. Cl.
CPC ........ *A61M 5/3204* (2013.01); *A61M 5/2033* (2013.01); *A61M 5/326* (2013.01); *A61M 5/5086* (2013.01); *A61M 2005/206* (2013.01); *A61M 2005/208* (2013.01); *A61M 2005/2013* (2013.01); *A61M 2005/3247* (2013.01); *A61M 2205/581* (2013.01); *A61M 2205/582* (2013.01); *A61M 2205/584* (2013.01)

(58) Field of Classification Search
CPC .... A61M 2005/2013; A61M 2005/206; A61M 2005/3247; A61M 5/2033; A61M 5/326
USPC ......................................................... 604/198
See application file for complete search history.

(56) References Cited

U.S. PATENT DOCUMENTS

2010/0249705 A1    9/2010    Kronestedt
2014/0207106 A1    7/2014    Bechmann

FOREIGN PATENT DOCUMENTS

EP    2 438 942    4/2012
EP    2 468 335    6/2012
(Continued)

OTHER PUBLICATIONS

Extended European Search Report in Application No. 13175662.9, dated Jan. 2, 2014, 8 pages.
(Continued)

*Primary Examiner* — Deanna K Hall
(74) *Attorney, Agent, or Firm* — Fish & Richardson P.C.

(57) ABSTRACT

An autoinjector includes a case having a rib, a needle shroud telescopically coupled to the case, a carrier slidably arranged in the case and adapted to hold a medicament container, and a collar rotatably and slidably disposed in the case and coupled to the needle shroud and the carrier. The needle shroud is movable between a first extended position, a retracted position and a locked second extended position. The carrier is movable from a first axial position to a second axial position relative to the case. The collar abuts the rib when the needle shroud is in the first extended position and the carrier is in the first axial position, and the collar disengages the rib when the needle shroud is in the retracted position and the carrier is in the second axial position.

15 Claims, 21 Drawing Sheets

(56) References Cited

FOREIGN PATENT DOCUMENTS

| EP | 2 489 380 | 8/2012 |
|---|---|---|
| JP | 2010-532189 | 10/2010 |
| WO | WO 2009/063030 | 5/2009 |
| WO | WO 2013/034984 | 3/2013 |

OTHER PUBLICATIONS

International Preliminary Report on Patentability in International Application No. PCT/EP2014/064425, dated Jan. 12, 2016, 8 pages.
International Search Report and Written Opinion in International Application No. PCT/EP2014/064425, dated Dec. 16, 2014, 12 pages.
Rote Liste, "50. Hypophysen-, Hypothalamushormone, andere regulatorische Peptide u. ihre Hemmstoffe," Chapter 50, ed. 2008, 20 pages.

AUTOINJECTOR

CROSS-REFERENCE TO RELATED APPLICATIONS

This application is a continuation of U.S. patent application Ser. No. 14/903,351, filed Jan. 7, 2016, which is a U.S. national stage application under 35 USC § 371 of International Application No. PCT/EP2014/064425, filed on Jul. 7, 2014, which claims priority to European Patent Application No. 13175662.9, filed on Jul. 9, 2013, the entire contents of which are incorporated herein by reference.

TECHNICAL FIELD

The invention relates to an autoinjector.

BACKGROUND

Administering an injection is a process which presents a number of risks and challenges for users and healthcare professionals, both mental and physical. Injection devices typically fall into two categories—manual devices and autoinjectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Further, the force required to push the button/plunger may be too high (e.g., if the user is elderly or a child). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

There remains a need for an improved autoinjector.

SUMMARY

It is an object of the present invention to provide an improved autoinjector.

In an exemplary embodiment, an autoinjector according to the present invention comprises a case having a rib, a needle shroud telescopically coupled to the case and movable between a first extended position, a retracted position and a locked second extended position, a carrier slidably arranged in the case, adapted to hold a medicament container, and movable from a first axial position to a second axial position relative to the case, and a collar rotatably and slidably disposed in the case and coupled to the needle shroud and the carrier. The collar abuts the rib when the needle shroud is in the first extended position and the carrier is in the first axial position, and the collar disengages the rib when the needle shroud is in the retracted position and the carrier is in the second axial position.

In an exemplary embodiment, the autoinjector further comprises a plunger slidably coupled to the carrier, and a drive spring biasing the plunger relative to the carrier. The carrier includes a compliant beam having a boss adapted to engage an opening in the plunger when the carrier is in the first axial position. The boss is adapted to engage the case when the carrier is in the second axial position.

In an exemplary embodiment, the collar includes a shroud boss adapted to engage a shroud slot in the needle shroud, a carrier boss adapted to engage a carrier slot in the carrier and a case boss adapted to engage the rib in the case. The shroud boss, the carrier boss and the case boss are disposed in approximately a same plane on the collar.

In an exemplary embodiment, the collar is in a first angular position relative to the case when the needle shroud is in the first extended position and the carrier is in the first axial position. The collar rotates to a second angular position relative to the case and translates proximally relative to the case when the needle shroud moves from the first extended position to the retracted position. The collar translates distally relative to the case when the needle shroud is in the retracted position and the carrier moves from the first axial position to the second axial position. The boss disengages the opening when the carrier is in the second axial position and wherein the plunger translates axially relative to the carrier under the force of the drive spring advancing the carrier from the second axial position to a third axial position relative to the case. The collar rotates to a third angular position relative to the case and translates with the needle shroud distally relative to the case when the carrier is in the third axial position. The collar rotates to a fourth angular position relative to the case when the needle shroud is in the locked second extended position. The shroud boss engages a shroud slot notch in the shroud slot and the carrier boss engages a carrier slot notch in the carrier slot when the collar is in the fourth angular position and the needle shroud is in the locked second extended position. The engagement of the carrier boss and the carrier slot notch substantially fixes the collar in an axial position relative to the case.

In an exemplary embodiment, the autoinjector further comprises a control spring biasing the collar relative to the case.

In an exemplary embodiment, the autoinjector further comprises a trigger button coupled to or integral with the carrier.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1A:
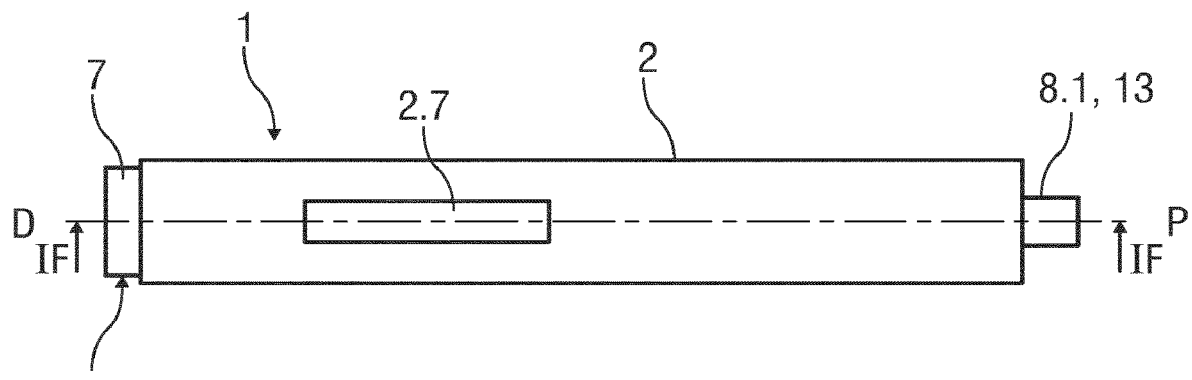
FIG. 1A is a side view of an exemplary embodiment of an autoinjector according to the present invention prior to use.
Figure 1B:
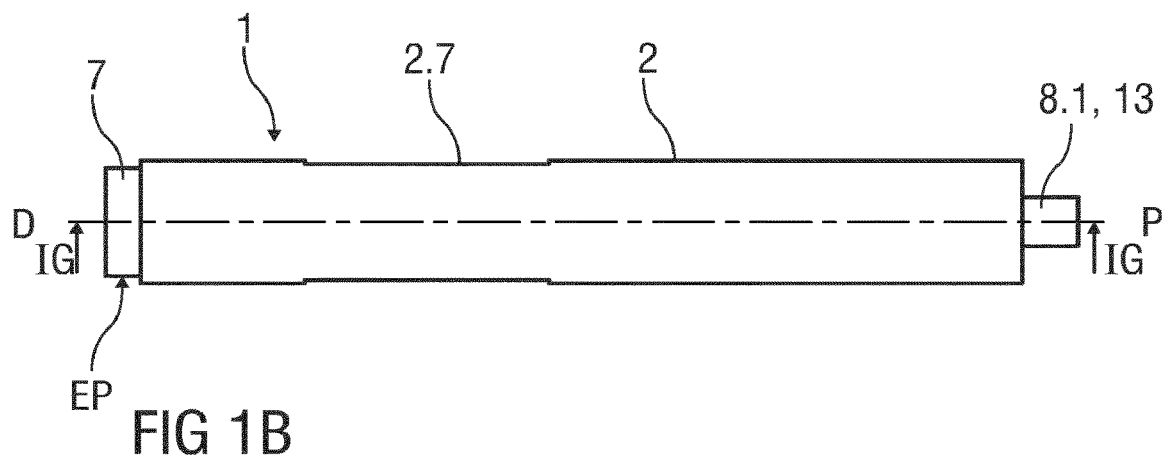
FIG. 1B is a side view of an exemplary embodiment of an autoinjector according to the present invention prior to use.
Figure 1C:
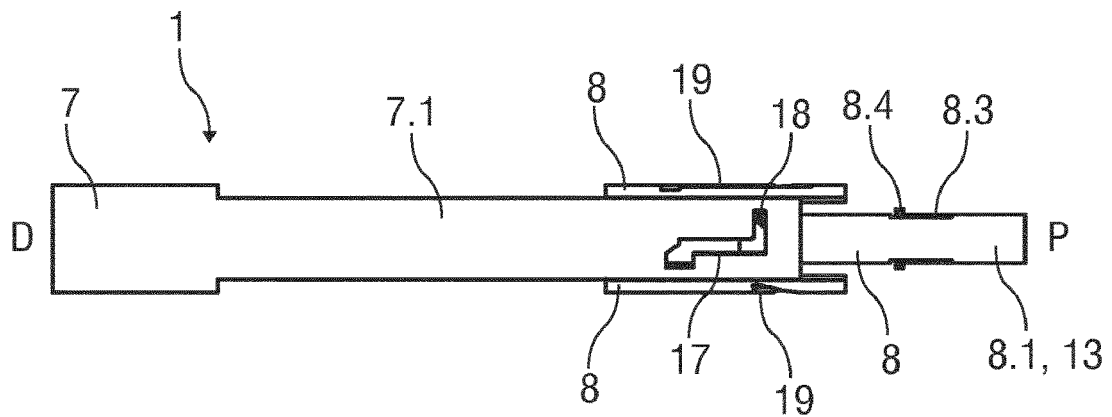
FIG. 1C is a side view of an exemplary embodiment of an autoinjector according to the present invention prior to use.
Figure 1D:
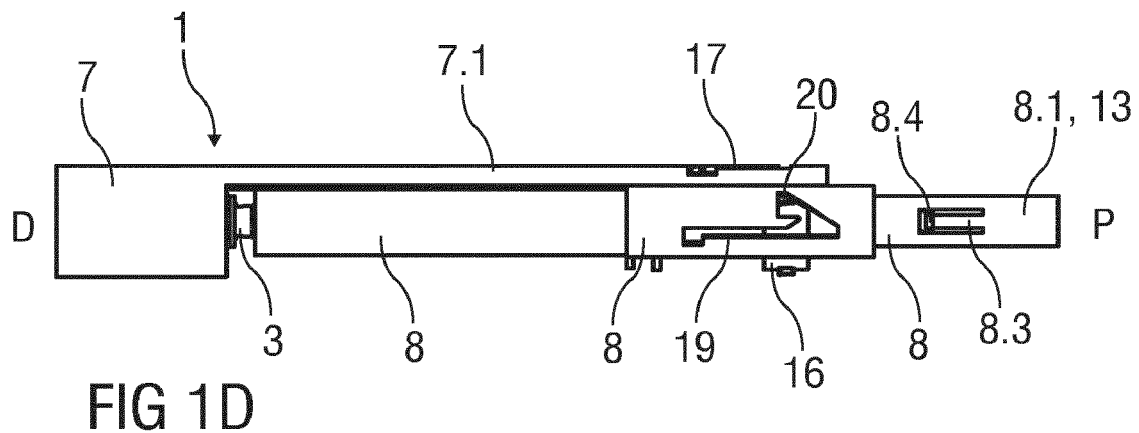
FIG. 1D is a side view of an exemplary embodiment of an autoinjector according to the present invention prior to use.
Figure 1E:
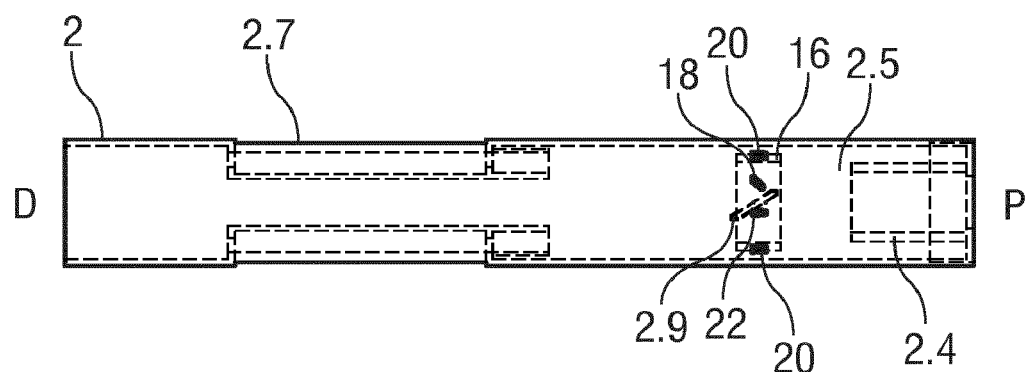
FIG. 1E is a semi-transparent side view of an exemplary embodiment of an autoinjector according to the present invention prior to use.
Figure 1F:
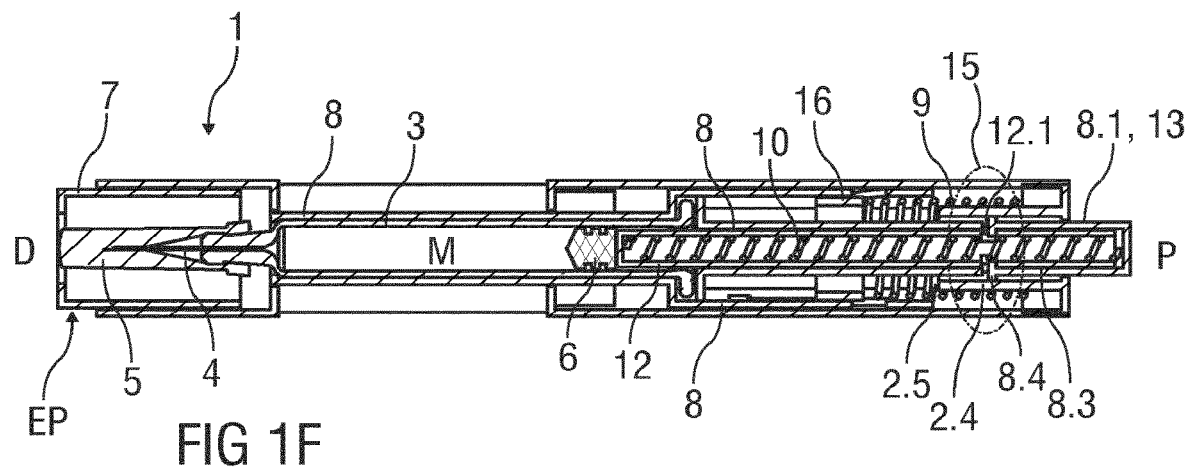
FIG. 1F is a longitudinal section of an exemplary embodiment of an autoinjector according to the present invention prior to use.
Figure 1G:
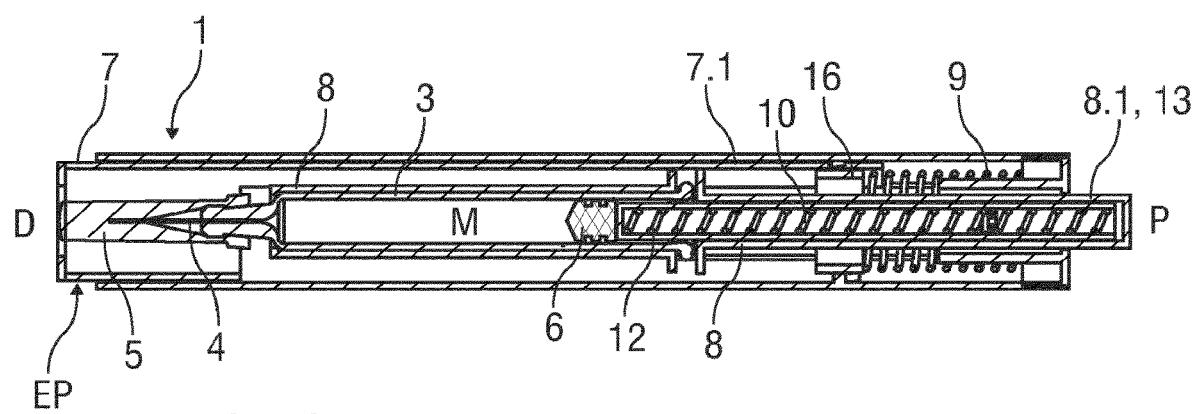
FIG. 1G is a longitudinal section of an exemplary embodiment of an autoinjector according to the present invention prior to use.

FIGS. 1A-1F and 1B are different views of an exemplary embodiment of an autoinjector 1 according to the present invention prior to use. In an exemplary embodiment, the autoinjector 1 includes a case 2 telescopically coupled to a needle shroud 7. FIGS. 1C and 1D are related side views of the autoinjector 1 with the case 2 removed for clarity. FIG. 1E is a related semi-transparent side view of the case 2. FIGS. 1F and 1G are related longitudinal sections of the autoinjector 1.

In an exemplary embodiment as shown in FIGS. 1F and 1G, the case 2 is adapted to receive a medicament container, such as a syringe 3 containing a medicament M. The syringe 3 may be a pre-filled syringe and have a needle 4 arranged at a distal end. When the autoinjector 1 or the syringe 3 is assembled, a protective needle sheath 5 is removably attached to the needle 4. A stopper 6 is arranged for sealing the syringe 3 proximally and for displacing the medicament M contained in the syringe 3 through the needle 4. In other exemplary embodiments, the medicament container may be a cartridge or an ampoule, and the needle 4 may be removably coupled to the medicament container. In an exemplary embodiment, the syringe 3 is held in a syringe carrier 8 and supported at its proximal end therein. The syringe carrier 8 is slidably arranged within the case 2.

In an exemplary embodiment, a cap (not illustrated) may be removably coupled to a distal end of the case 2. The case 2 may include a viewing window 2.7 for providing visual access to contents of the syringe 3.

In an exemplary embodiment, the needle shroud 7 is telescoped in the distal end of the case 2. A control spring 9 is arranged to bias the needle shroud 7 in a distal direction D relative to the case 2.

In an exemplary embodiment, a drive spring 10 (which may be a compression spring) is arranged within a proximal part 8.1 of the syringe carrier 8. A plunger 12 serves for forwarding a force of the drive spring 10 to the stopper 6. In an exemplary embodiment, the plunger 12 is hollow and telescoped within the proximal part 8.1 of the syringe carrier 8 wherein the drive spring 10 is arranged within the plunger 12 biasing the plunger 12 in the distal direction D relative to the syringe carrier 8. In an exemplary embodiment, the proximal part 8.1 of the syringe carrier 8 protrudes through an opening in a proximal end of the case 2 and serves as a trigger button 13. In other exemplary embodiments, a button overmold may be coupled to or integralled formed with the trigger button 13.

In an exemplary embodiment, a plunger release mechanism 15 is arranged for preventing release of the plunger 12 prior to the needle 4 reaching an insertion depth and for releasing the plunger 12 once the needle 4 reaches its insertion depth. The plunger release mechanism 15 may comprise one or more compliant beams 8.3 with a respective first boss 8.4 arranged on the syringe carrier 8, a respective first opening 12.1 (best seen in FIG. 5F) laterally arranged in the plunger 12 for engaging the first boss 8.4, a proximal narrow section 2.4 of the case 2 adapted to radially outwardly support the first boss 8.4 and prevent it from disengaging the first opening 12.1, a wide section 2.5 in the case 2 distal of the narrow section 2.4 adapted to allow radially outward deflection of the first boss 8.4 once the first boss 8.4 is axially aligned with the wide section 2.5. At least one of the first boss 8.4 and the first opening 12.1 may be ramped such that the plunger 12 under load from the drive spring 10 deflects the first boss 8.4 radially outwards.

In an exemplary embodiment, a control mechanism 21 (best seen in FIGS. 2A to 2I) is arranged for selectively applying the force of the control spring 9 to the syringe carrier 8 or to the needle shroud 7. Furthermore, the control mechanism 21 is arranged for locking the trigger button 13 such that it cannot be operated prior to depression of the needle shroud 7 against an injection site and for unlocking the trigger button 13 on depression of the needle shroud 7 against the injection site, thus allowing operation of the trigger button 13.

In an exemplary embodiment, the control mechanism 21 comprises a collar 16 having a shroud boss 18 adapted to engage a shroud slot 17 in the needle shroud 7, a carrier boss 20 adapted to engage a carrier slot 19 in the syringe carrier 8, and a case boss 22 adapted to engage an angled case rib 2.9 on the case 2.

In an exemplary embodiment, the control spring 9 is proximally grounded in the case 2 and distally bears against the collar 16 which is movable axially and rotationally relative to the case 2. In the initial state prior to use, the control spring 9 may be compressed between the case 2 and the collar 16.

FIGS. 2A to 2I are schematic views of exemplary embodiments of the components of the control mechanism 21 corresponding to different states of operation of the autoinjector 1. Although the case boss 22, the carrier boss 20 and the shroud boss 18 are shown at different axial positions for clarity in FIGS. 2A to 2I, in an exemplary embodiment, all of the bosses 18, 20, 22 on the collar 16 are disposed in the same plane as shown in FIG. 1E. In an exemplary embodiment, the shroud slot 17 comprises a transversal first surface 17.1, a transversal second surface 17.2, a longitudinal third surface 17.3, a transversal fourth surface 17.4, an angled fifth surface 17.5, a transversal sixth surface 17.6 and a transversal seventh surface 17.7. In an exemplary embodiment, the carrier slot 19 comprises a transversal first surface 19.1, an angled second surface 19.2, an angled third surface 19.3, a longitudinal fourth surface 19.4 and a transversal fifth surface 19.5.

Figure 2A:
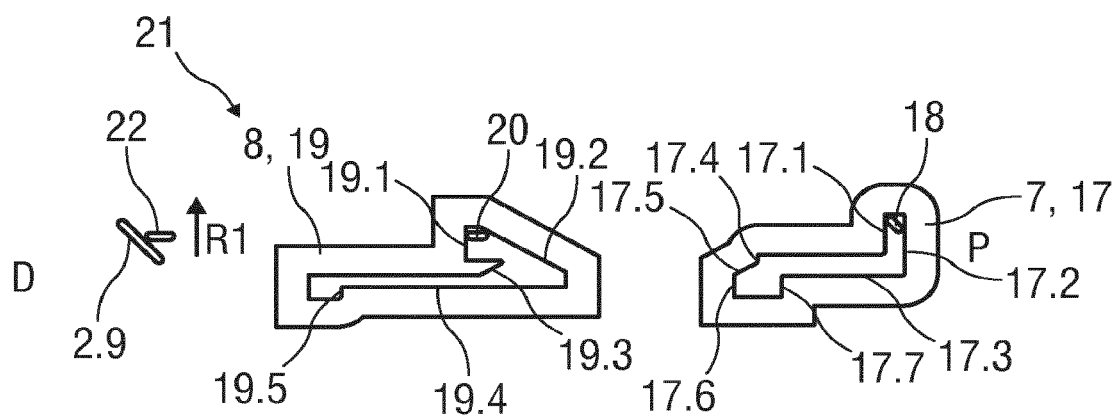
FIGS. 2A to 2I are schematic views of an exemplary embodiment of a control mechanism for an autoinjector according to the present invention.

A exemplary sequence of operation of the autoinjector 1 is as follows:

Prior to use the autoinjector 1 is in the state as illustrated in FIGS. 1A to 1G, and the control mechanism 21 is in the state illustrated in FIG. 2A. If applicable, the autoinjector 1 is removed from a packaging. The medicament M in the syringe 3 may be visually examined through the viewing window 2.7.

If the cap (not illustrated) is attached to the case 2 and/or the protective needle sheath 5, the cap may be removed by pulling it in the distal direction D away from the case 2 thereby also removing the protective needle sheath 5 from the needle 4. The load exerted by pulling the cap 11 is resolved in the case 2, because the case boss 22 on the collar 16 abuts the angled case rib 2.9 in the distal direction D. The collar 16 is in a first angular position relative to the case 2. As the case rib 2.9 is angled, a rotational force in a first rotational direction R1 and an axial force in the distal direction D are applied to the collar 16 due to the control spring 9 biasing the collar 16 in the distal direction D. The rotational and axial forces are resolved by the shroud boss 18 abutting the shroud slot 17 and/or the carrier boss 20 abutting the carrier slot 19 (in the illustrated embodiment both are used) such that the collar 16 cannot rotate or translate axially relative to the case 2. The syringe carrier 8 is in a first axial position relative to the case 2.

Movement of the syringe carrier 8 in the distal direction D is prevented by the carrier boss 20 being in contact with the angled second surface 19.2 of the carrier slot 19. Thus, depression of the trigger button 13 is prevented. Movement of the syringe carrier 8 in the proximal direction P is prevented by a backstop (not illustrated) on the case 2. Furthermore, the force of the control spring 9 on the collar 16 prevents the syringe carrier 8 from moving in the proximal direction P.

The needle shroud 7 is in a first extended position EP, protruding from the case 2 in the distal direction D. The extension of the needle shroud 7 distally beyond the case 2 is limited by the shroud boss 18 abutting the transversal first surface 17.1 and the transversal second surface 17.2 on the shroud slot 17. Due to the collar 16 being prevented from moving in the distal direction D by the case rib 2.9, the needle shroud 7 cannot move in the distal direction D either. Movement of the needle shroud 7 in the proximal direction P relative to the case 2 results in a corresponding axial translation of the collar 16 relative to the case 2, compressing the control spring 9.

The plunger release mechanism 15 prevents the plunger 12 from being released.

When the autoinjector 1 is pressed against an injection site, the needle shroud 7 is pressed into the case 2 into a retracted position RP against the force of the control spring 9.

Figure 2B:
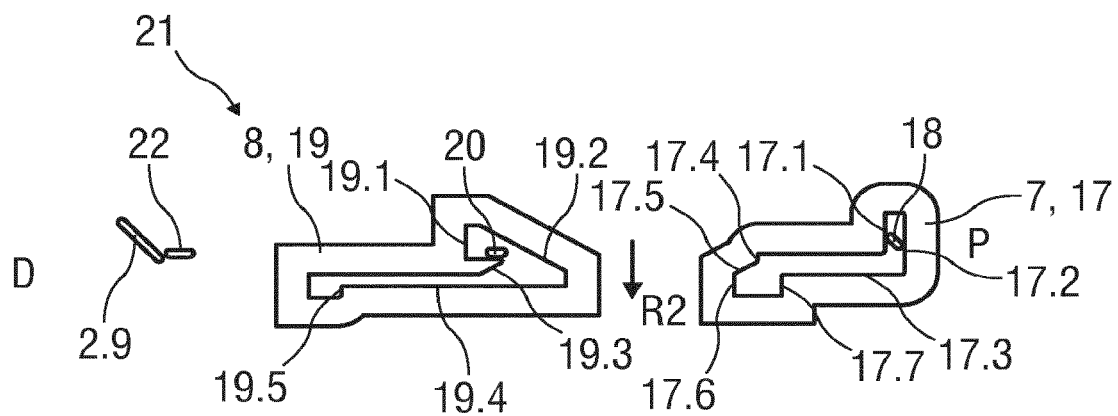
Figure 2C:
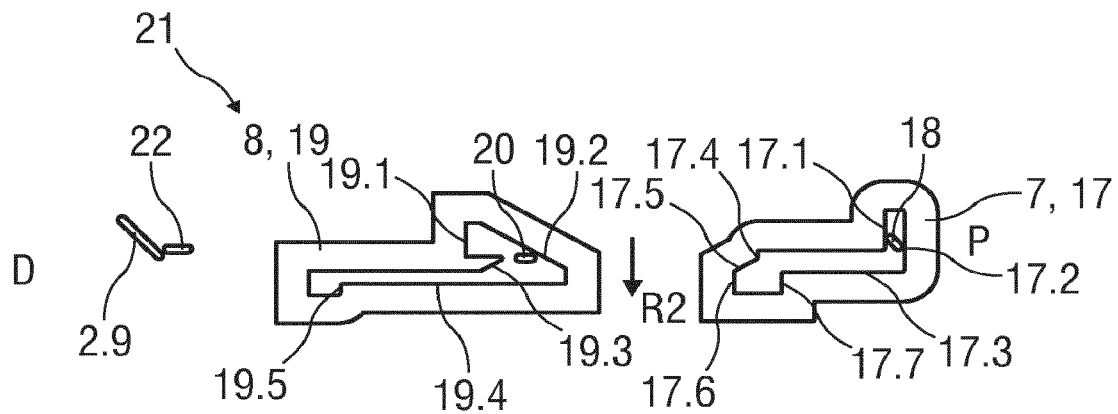
Figure 2D:
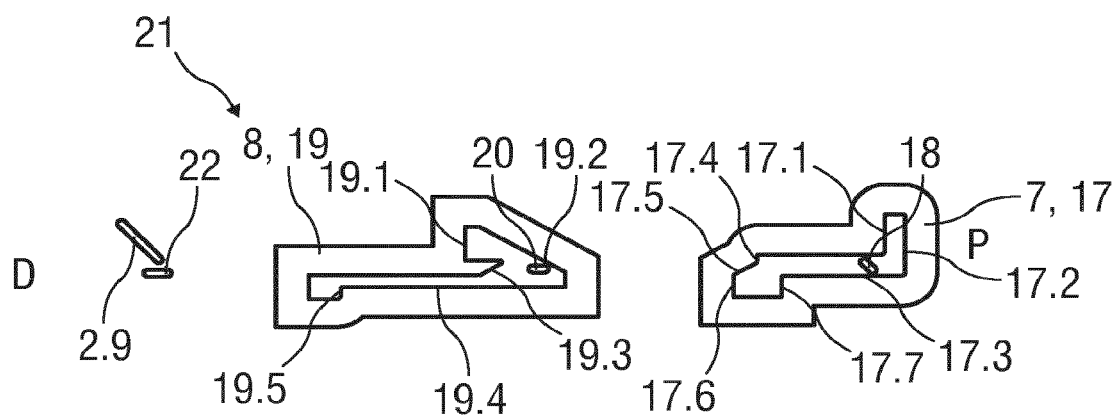
Figure 2E:
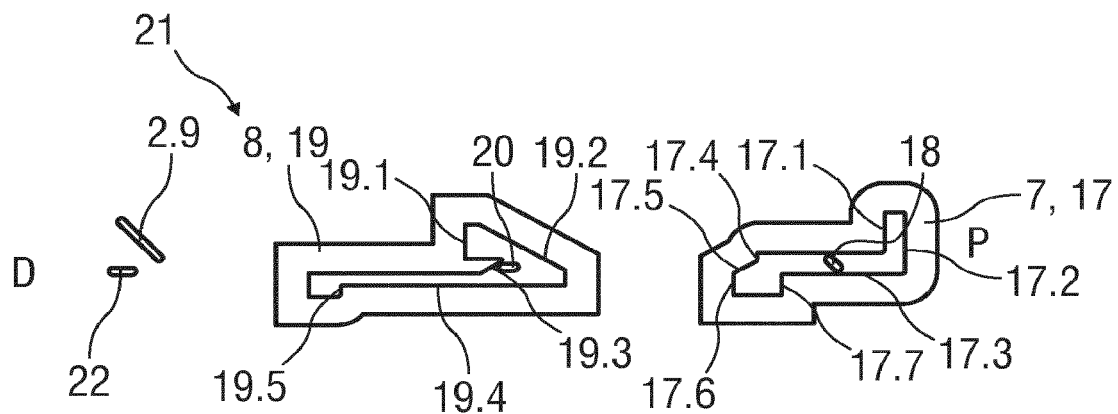
Figure 3A:
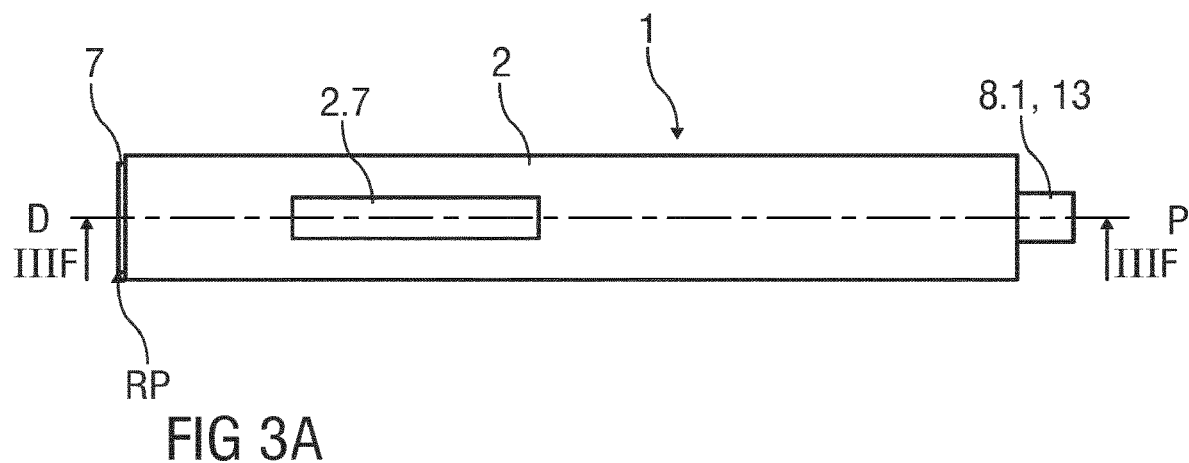
FIG. 3A is a side view of an exemplary embodiment of an autoinjector according to the present invention during use.
Figure 3B:
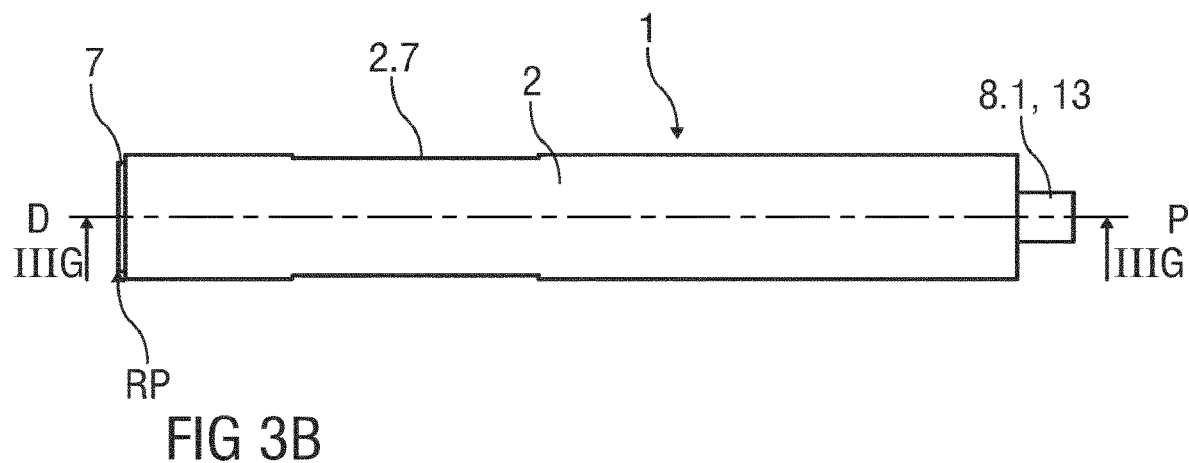
FIG. 3B is a side view of an exemplary embodiment of an autoinjector according to the present invention during use.
Figure 3C:
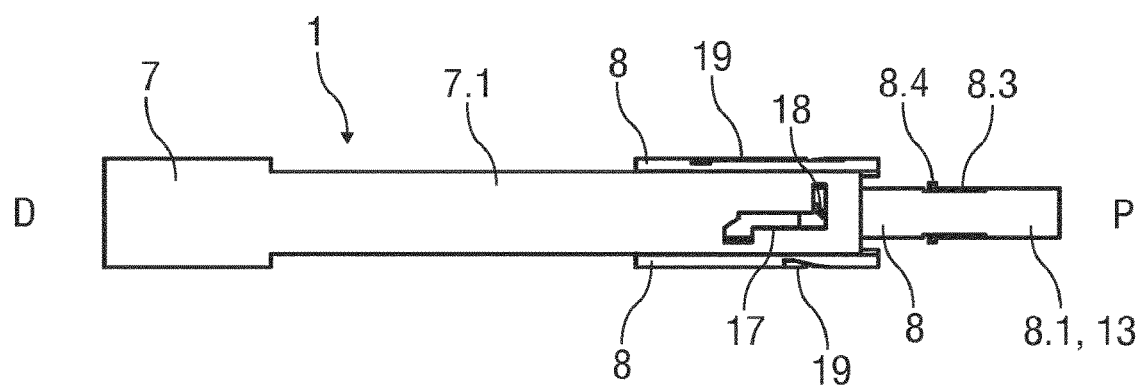
FIG. 3C is a side view of an exemplary embodiment of an autoinjector according to the present invention during use.
Figure 3D:
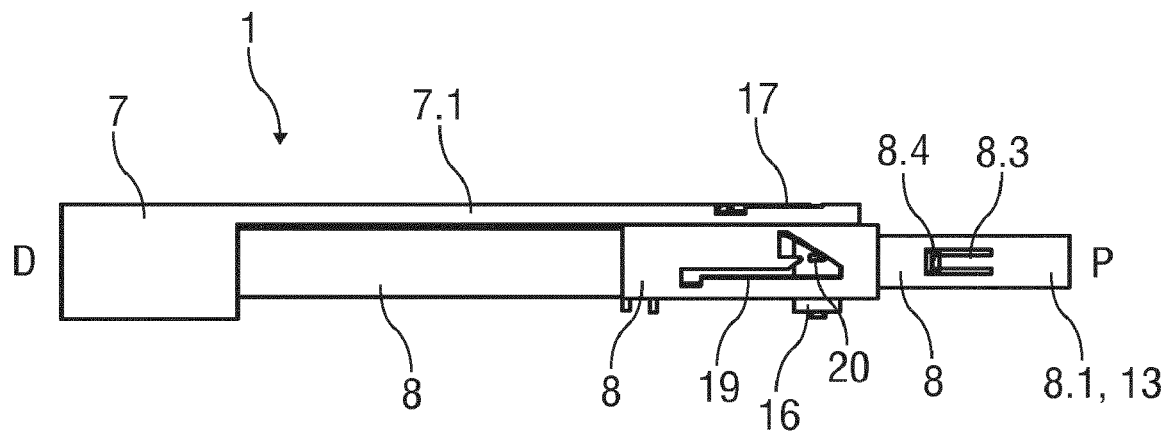
FIG. 3D is a side view of an exemplary embodiment of an autoinjector according to the present invention during use.
Figure 3E:
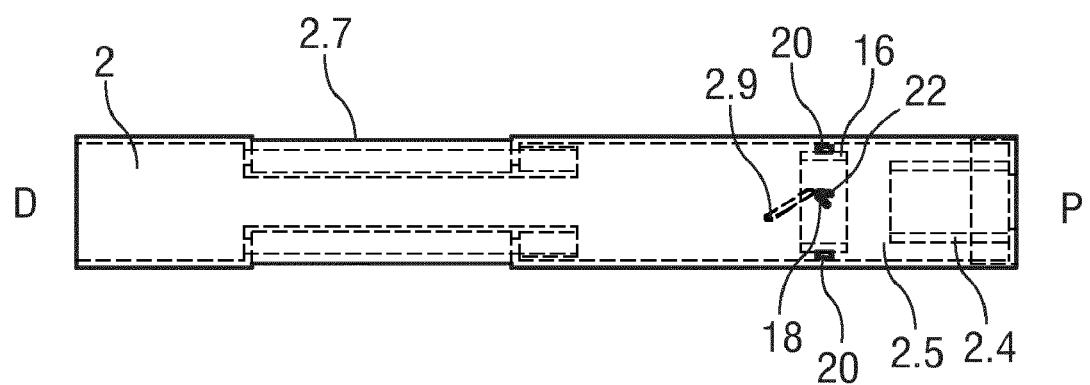
FIG. 3E is a semi-transparent side view of an exemplary embodiment of an autoinjector according to the present invention during use.
Figure 3F:
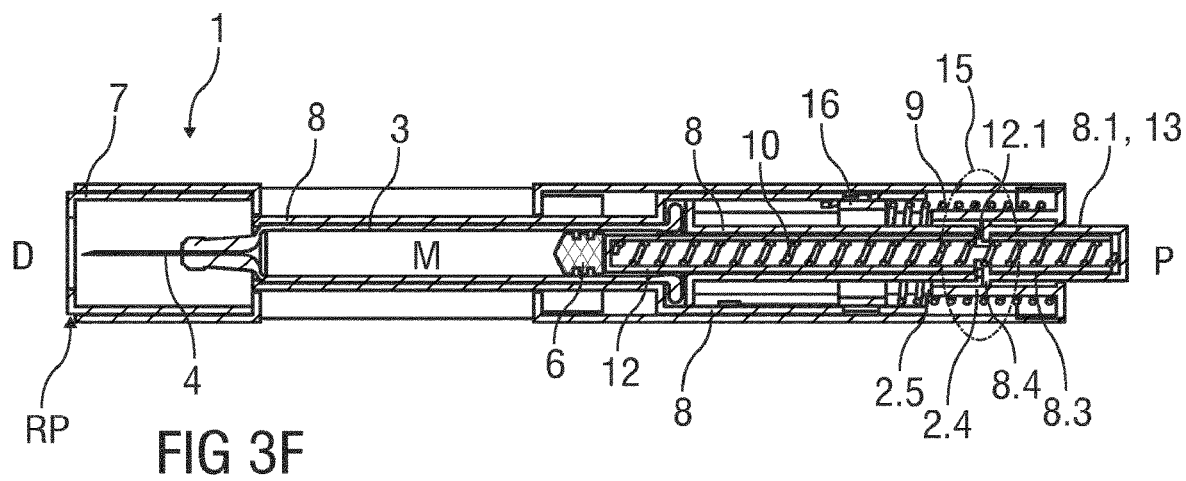
FIG. 3F is a longitudinal section of an exemplary embodiment of an autoinjector according to the present invention during use.
Figure 3G:
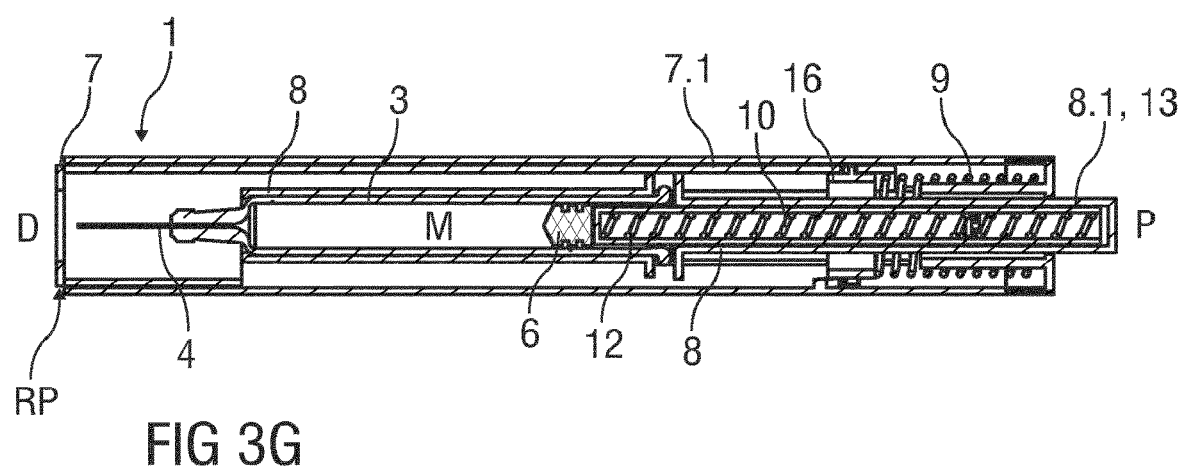
FIG. 3G is a longitudinal section of an exemplary embodiment of an autoinjector according to the present invention during use.

FIGS. 3A and 3B are different views of an exemplary embodiment of the autoinjector 1 with the needle shroud 7 in the retracted position RP. FIGS. 3C and 3D are related side views of the autoinjector 1 with the case 2 removed for clarity. FIG. 3E is a related semi-transparent side view of the case 2 with the collar 16. FIGS. 3F and 3G are related longitudinal sections of the autoinjector 1. FIG. 2B shows the control mechanism 21 as the needle shroud 7 is translating from the extended position EP to the retracted position RP. FIG. 2C shows the control mechanism 21 when the needle shroud 7 is in the retracted position RP.

The force opposing depression of the needle shroud 7 is provided by the control spring 9 through the collar 16 and the shroud boss 18 engaging the transversal first surface 17.1. During depression of the needle shroud 7 towards the retracted position RP, the shroud boss 18 abuts the transversal first surface 17.1 of the shroud slot 17 (cf. FIG. 2B) causing the collar 16 to translate axially in the proximal direction P relative to the case 2. The carrier boss 20 disengages the transversal first surface 19.1 of the carrier slot 19 in the proximal direction P. As the angled second surface 19.2 of the carrier slot 19 is angled relative to a transverse axis of the case 2, a rotational force is applied to the collar 16 in a second rotational direction R2 opposite the first rotational direction R1, causing the collar 16 to rotate to a second angular position relative to the case 2. If the autoinjector 1 were removed from the injection site, the collar 16 and needle shroud 7 would return in the distal direction D into the positions shown in FIGS. 1A to 1G and the control mechanism 21 would return into the state shown in FIG. 2A due to the engagement of the case boss 22 to the angled case rib 2.9 applying the rotational force to the collar 16 in the first rotational direction R1.

When the needle shroud 7 is in the retracted position RP, the case boss 22 remains abutting the case rib 2.9 (cf. FIG. 3E) and the shroud boss 18 remains abutting the transversal first surface 17.1 of the shroud slot 17 (cf. FIG. 3C). Thus, the collar 16 is prevented from moving axially relative to the case 2.

Figure 4A:
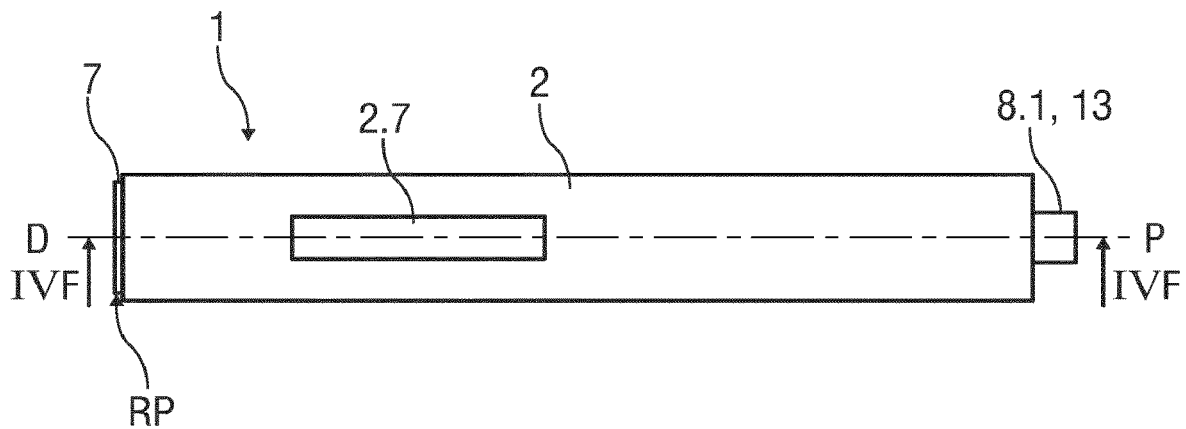
FIG. 4A is a side view of an exemplary embodiment of an autoinjector according to the present invention during use.
Figure 4B:
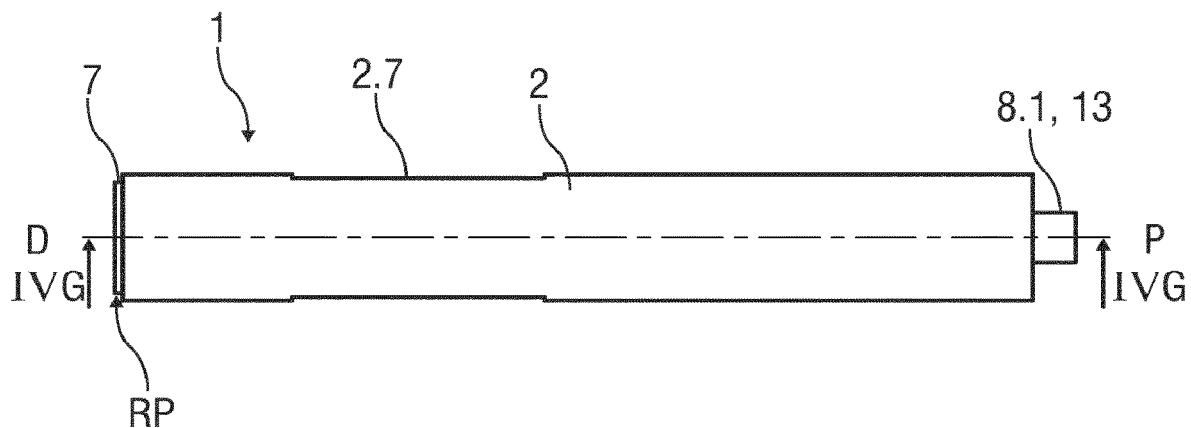
FIG. 4B is a side view of an exemplary embodiment of an autoinjector according to the present invention during use.
Figure 4C:
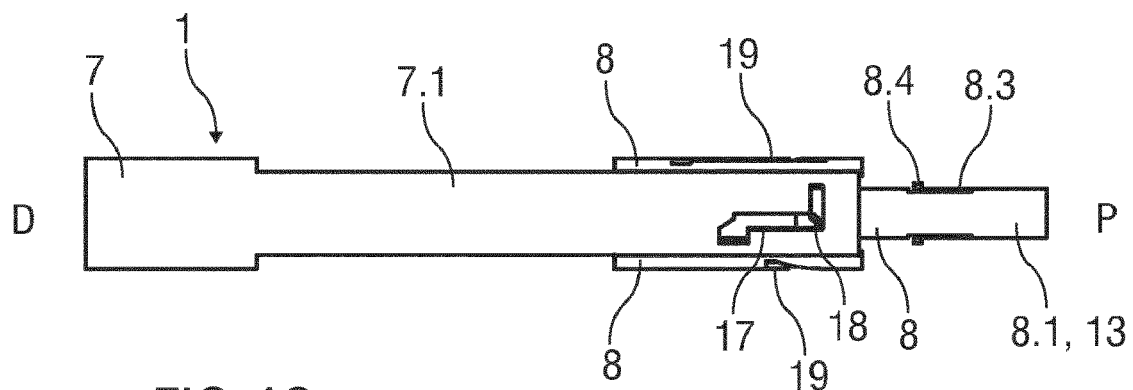
FIG. 4C is a side view of an exemplary embodiment of an autoinjector according to the present invention during use.
Figure 4D:
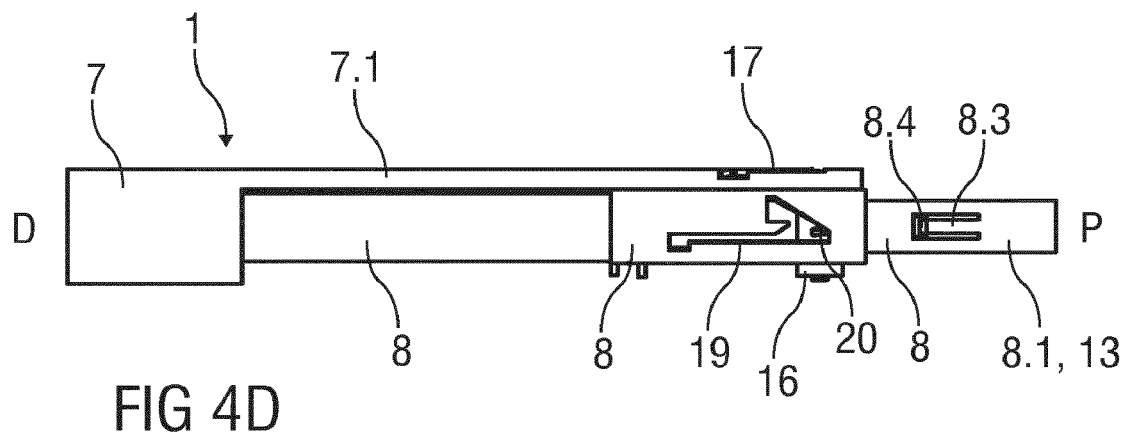
FIG. 4D is a side view of an exemplary embodiment of an autoinjector according to the present invention during use.
Figure 4E:
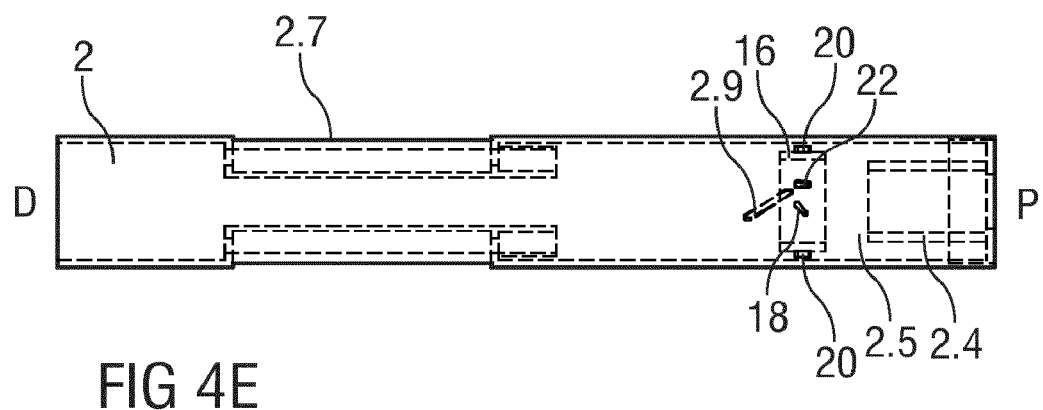
FIG. 4E is a semi-transparent side view of an exemplary embodiment of an autoinjector according to the present invention during use.
Figure 4F:
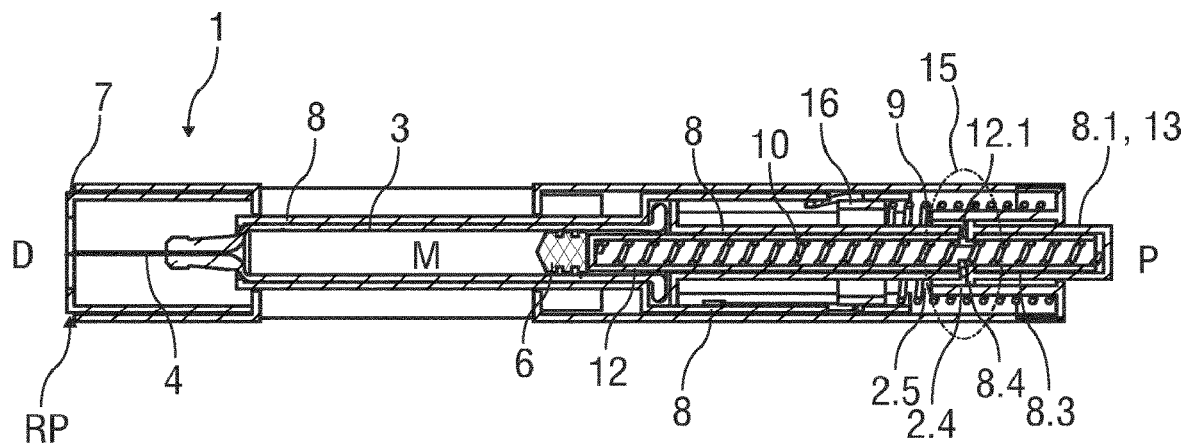
FIG. 4F is a longitudinal section of an exemplary embodiment of an autoinjector according to the present invention during use.
Figure 4G:
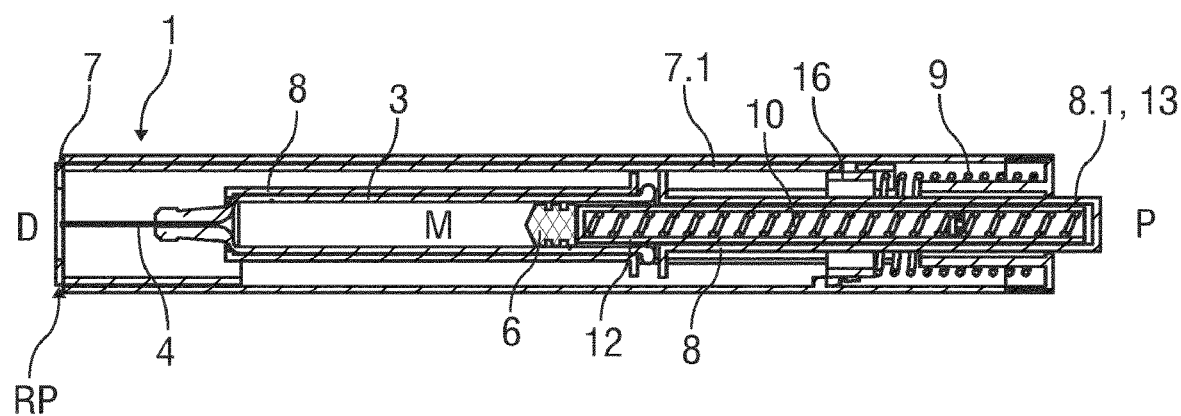
FIG. 4G is a longitudinal section of an exemplary embodiment of an autoinjector according to the present invention during use.

FIGS. 4A and 4B are different side views of an exemplary embodiment of the autoinjector 1 after depression of the trigger button 13. FIGS. 4C and 4D are related side views of the autoinjector 1 with the case 2 removed for clarity. FIG. 4E is a related semi-transparent side view of the case 2 with the collar 16. FIGS. 4F and 4G are related longitudinal sections of the autoinjector 1.

When the trigger button 13 is pressed, the syringe carrier 8 moves in the distal direction D from the first axial position to a second axial position relative to the case 2, causing the carrier boss 20 to ride further along the angled second surface 19.2 and thereby rotating the collar 16 relative to the case 2 in the second rotational direction R2 to a third angular position relative to the case 2. After sufficient rotation of the collar 16 relative to the case 2, the shroud boss 18 comes clear of the transversal first surface 17.1 of the shroud slot 17, and the case boss 22 comes clear of the case rib 2.9. As the collar 16 is thus axially neither supported by the case 2 nor by the shroud slot 17, the collar 16 moves in the distal direction D guided by the shroud boss 18 along the longitudinal third surface 17.3 (cf. FIG. 2D), wherein the carrier boss 20 disengages the angled second surface 19.2 and moves in the distal direction D towards the angled third surface 19.3 of the carrier slot 19. As the carrier boss 20 engages the angled third surface 19.3 of the carrier slot 19, a rotational force in the second rotational direction R2 is applied to the collar 16 which is resolved by the shroud boss 18 abutting the third longitudinal surface 17.3 such that the carrier boss 20 cannot disengage the angled third surface 19.3. The collar 16 and the control spring 9 are thus axially coupled to the syringe carrier 8. The control spring 9 coupled to the syringe carrier 8 through the collar 16 advances the syringe carrier 8 from the second axial position to a third axial position in the distal direction D relative to the case 2 such that the needle 4 is extended from the case 2 and inserted into the injection site.

Figure 5A:
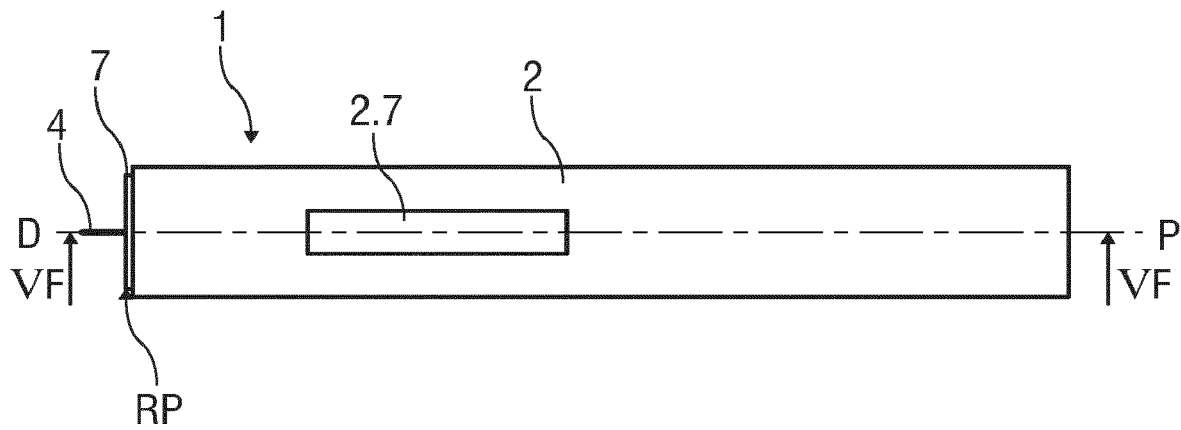
FIG. 5A is a side view of an exemplary embodiment of an autoinjector according to the present invention during use.
Figure 5B:
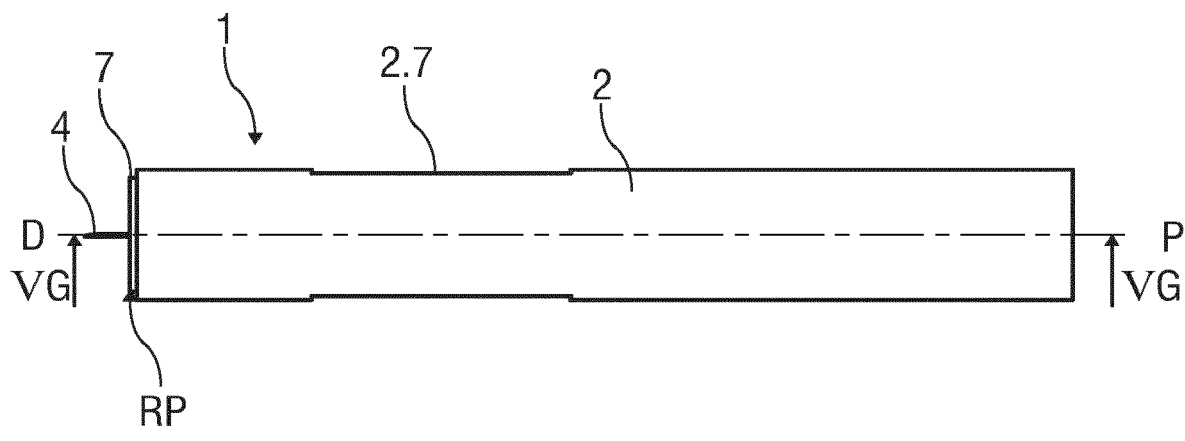
FIG. 5B is a side view of an exemplary embodiment of an autoinjector according to the present invention during use.
Figure 5C:
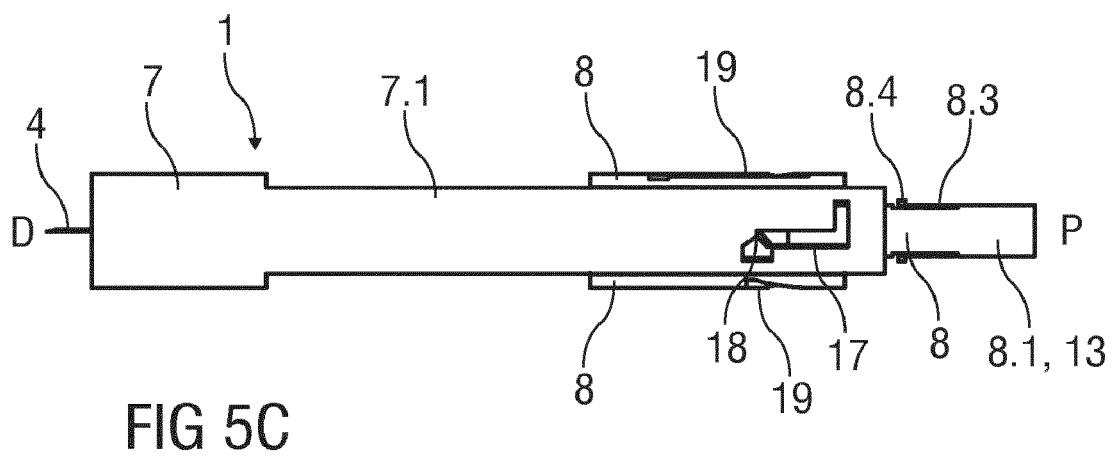
FIG. 5C is a side view of an exemplary embodiment of an autoinjector according to the present invention during use.
Figure 5D:
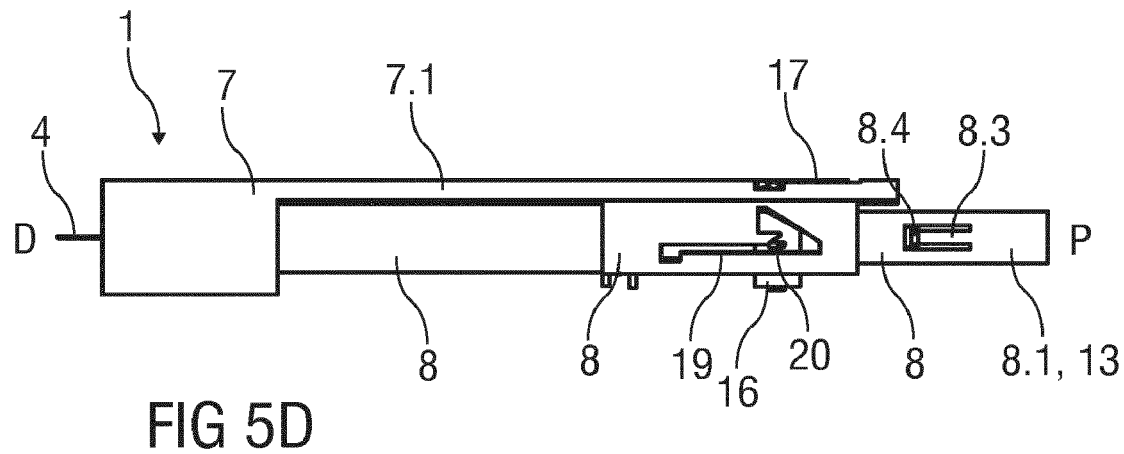
FIG. 5D is a side view of an exemplary embodiment of an autoinjector according to the present invention during use larity.
Figure 5E:
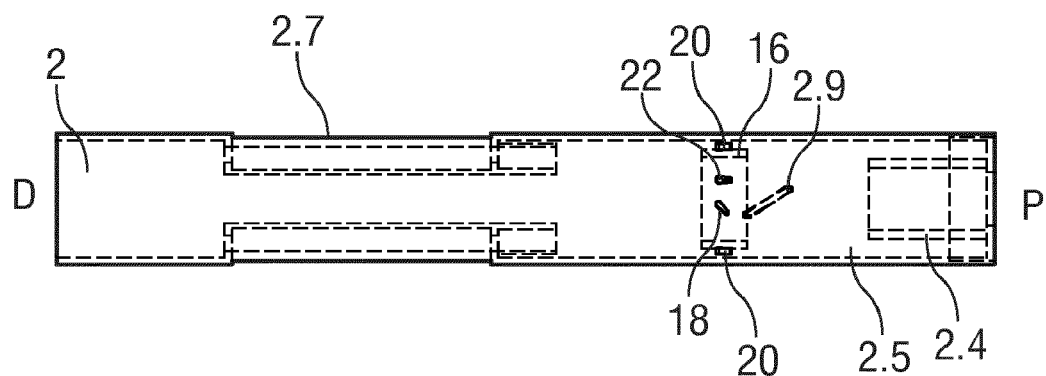
FIG. 5E is a semi-transparent side view of an exemplary embodiment of an autoinjector according to the present invention during use.
Figure 5F:
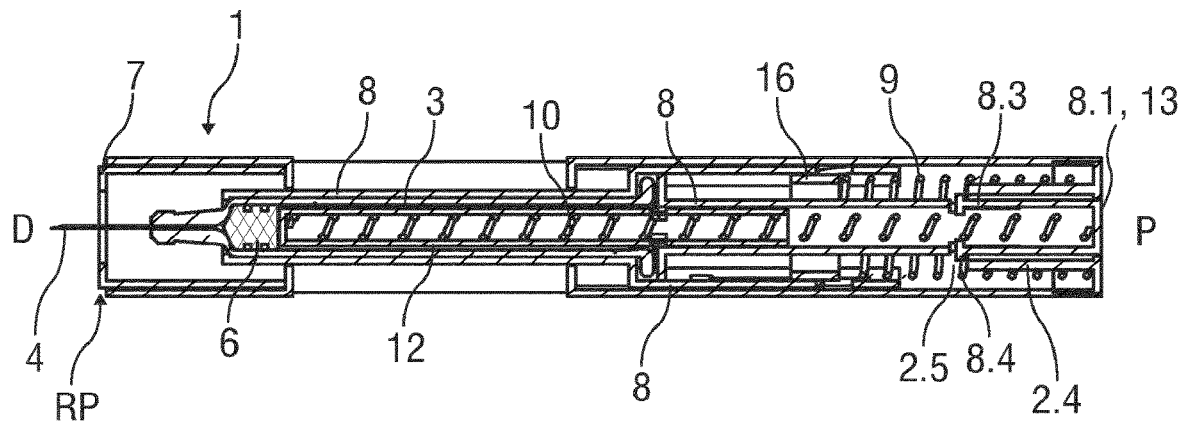
FIG. 5F is a longitudinal section of an exemplary embodiment of an autoinjector according to the present invention during use.
Figure 5G:
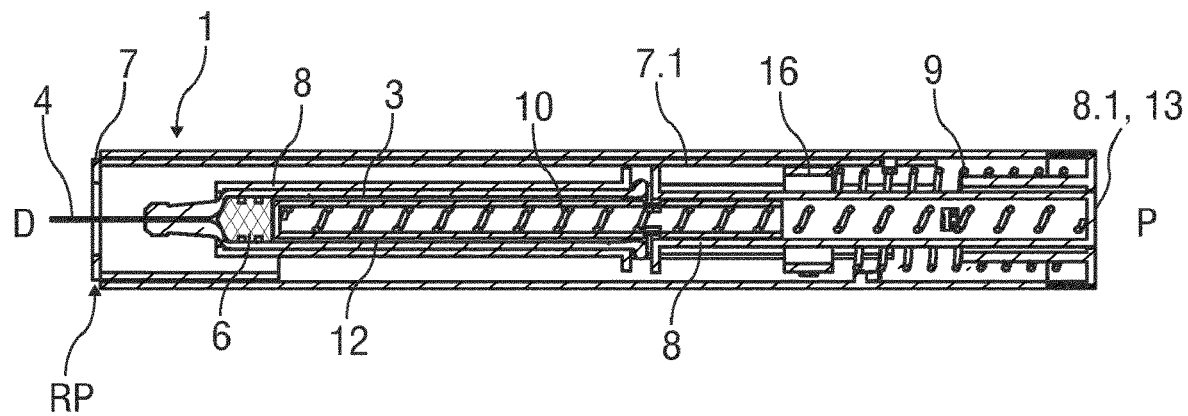
FIG. 5G is a longitudinal section of an exemplary embodiment of an autoinjector according to the present invention during use.

FIGS. 5A and 5B are different side views of an exemplary embodiment of the autoinjector 1 with the needle 4 extending from the case 2. FIGS. 5C and 5D are related side views of the autoinjector 1 with the case 2 removed for clarity. FIG. 5E is a related semi-transparent side view of the case 2 with the collar 16. FIGS. 5F and 5G are related longitudinal sections of the autoinjector 1.

Figure 2F:
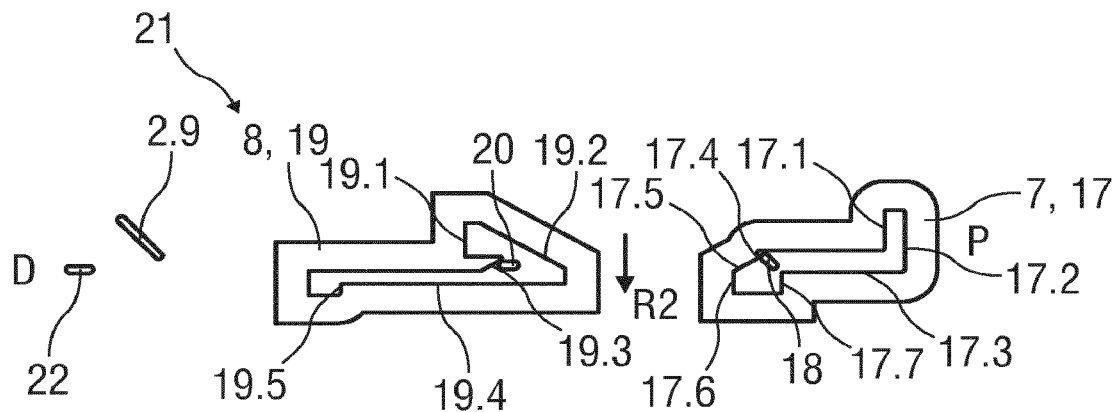
Figure 2G:
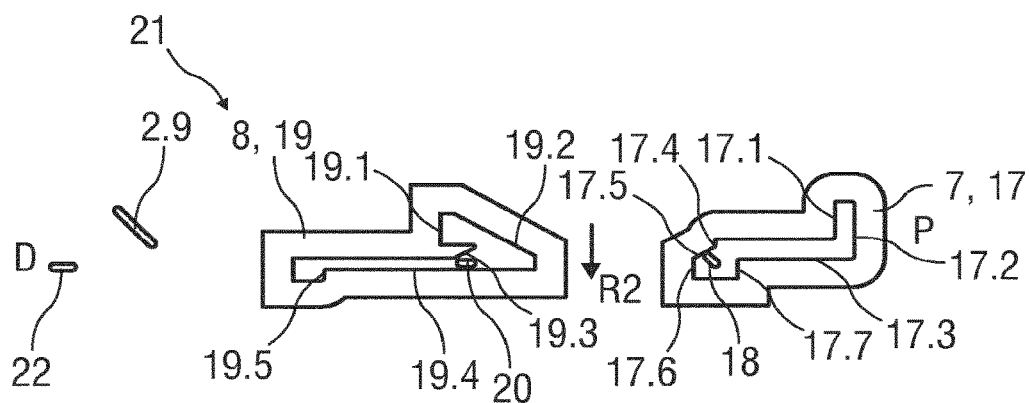

The translation of the syringe carrier 8 relative to the case 2 is limited when the shroud boss 18 abuts the transversal fourth surface 17.4 of the shroud slot 17 (cf. FIG. 2F). The transversal fourth surface 17.4 thus defines a penetration depth of the needle 4.

In an exemplary embodiment, prior to the shroud boss 18 abutting the transversal fourth surface 17.4 of the shroud slot 17, the plunger 12 is released by the plunger release mechanism 15. As the syringe carrier 8 translates in the distal direction D relative to the case 2, the compliant beams 8.3 reach the wide section 2.5, and the plunger 12, under load from the drive spring 10, deflects the first boss 8.4 on the compliant beam 8.3 radially outwards such that the first boss 8.4 disengages the first opening 12.1 in the plunger 12. The plunger 12 is thus released and advanced by the drive spring 10 displacing the stopper 6 within the syringe 3 and ejecting the medicament M through the needle 4. The release of the plunger release mechanism 15 may provide an audible and/or tactile feedback to the user. The progress of delivery of the medicament M can be observed through the viewing window 2.7 by examining the movement of the plunger 12 within the syringe 3. The plunger 12 is visible in the viewing window 2.7 thus helping the user differentiate between a used and an un-used autoinjector 1.

If the autoinjector 1 is removed from the injection site at any time after the needle 4 has reached insertion depth, the needle shroud 7 moves in the distal direction D driven by the control spring 9 which is coupled to the needle shroud 7 through the collar 16 and the shroud boss 18 abutting the transversal fourth surface 17.4 of the shroud slot 17.

Figure 6A:
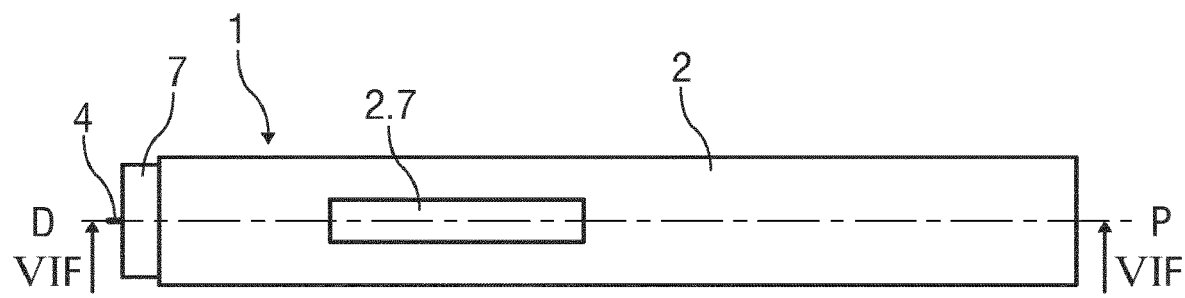
FIG. 6A is a side view of an exemplary embodiment of an autoinjector according to the present invention during use.
Figure 6B:
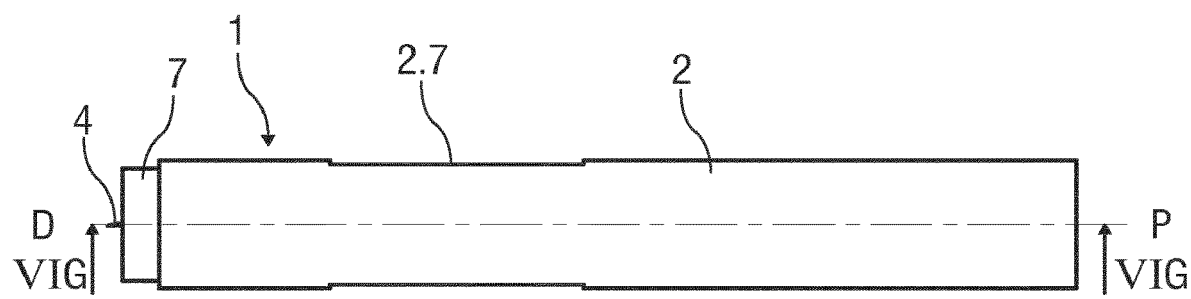
FIG. 6B is a side view of an exemplary embodiment of an autoinjector according to the present invention during use.
Figure 6C:
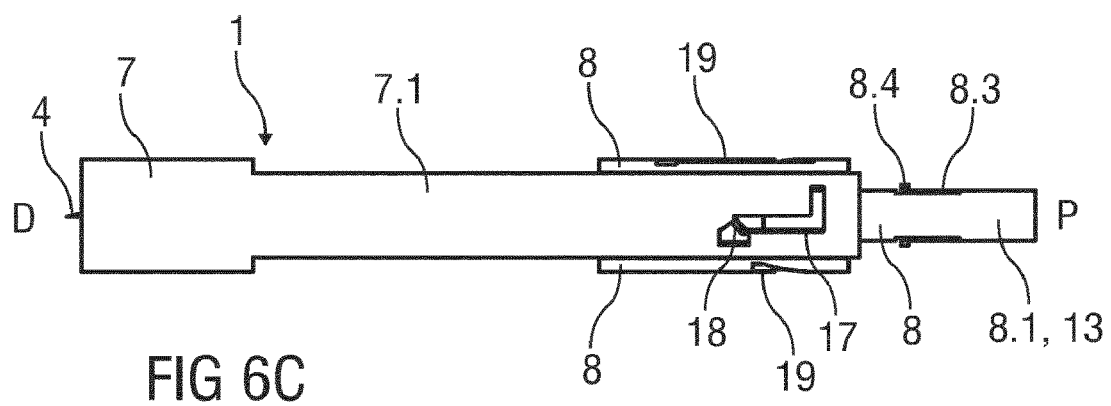
FIG. 6C is a side view of an exemplary embodiment of an autoinjector according to the present invention during use.
Figure 6D:
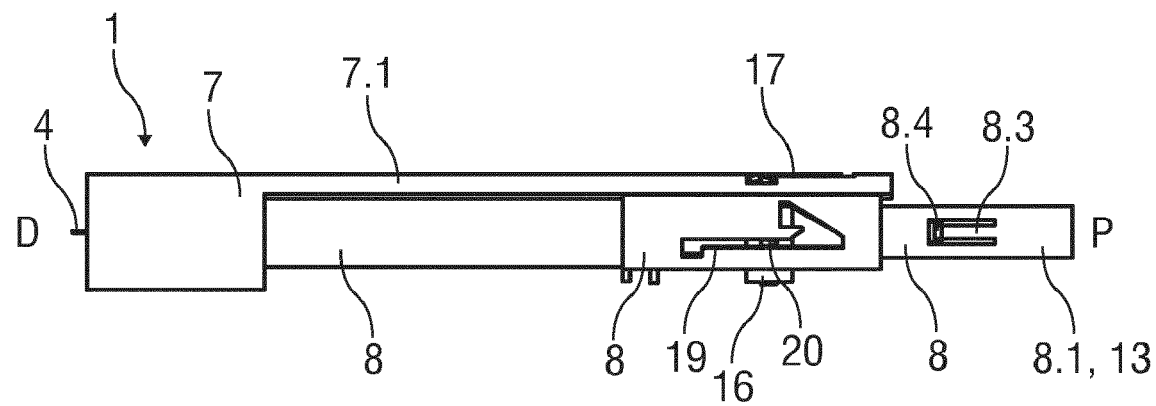
FIG. 6D is a side view of an exemplary embodiment of an autoinjector according to the present invention during use.
Figure 6E:
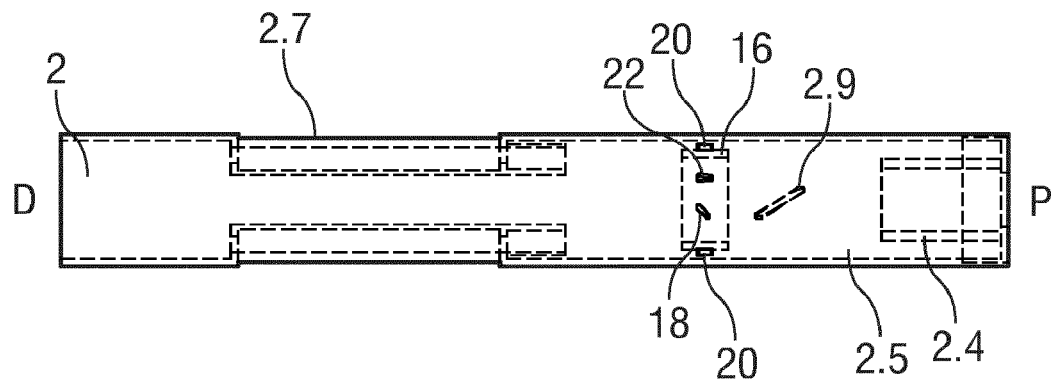
FIG. 6E is a semi-transparent side view of an exemplary embodiment of an autoinjector according to the present invention during use.
Figure 6F:
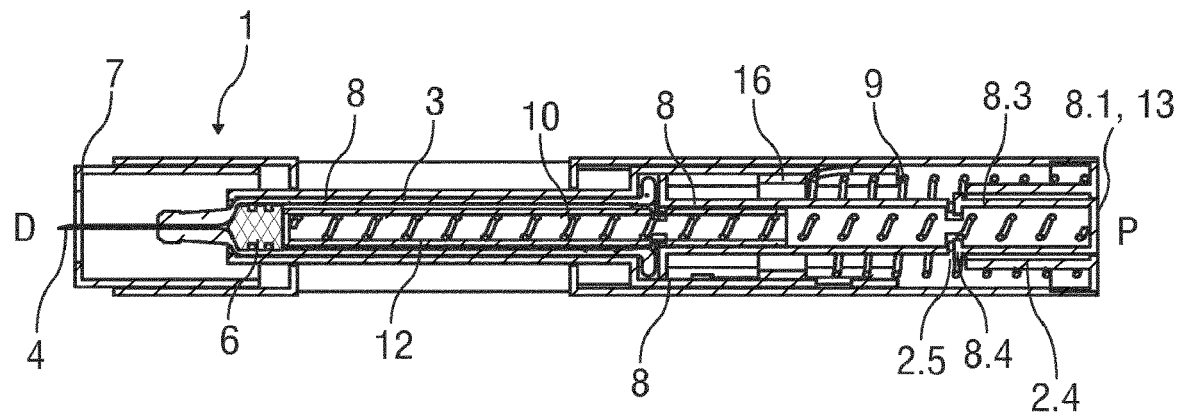
FIG. 6F is a longitudinal section of an exemplary embodiment of an autoinjector according to the present invention during use.
Figure 6G:
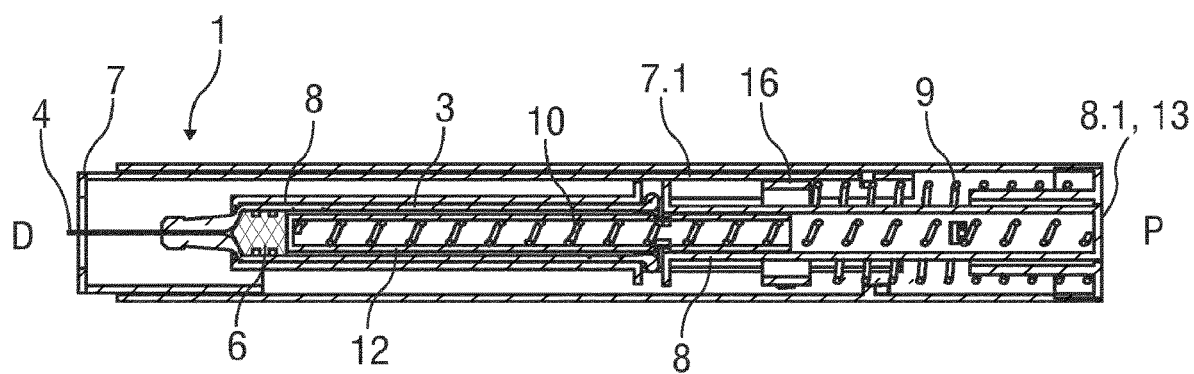
FIG. 6G is a longitudinal section of an exemplary embodiment of an autoinjector according to the present invention during use.

FIGS. 6A and 6B are different side views of an exemplary embodiment of the autoinjector 1 with the syringe 3 emptied. FIGS. 6C and 6D are related side views of the autoinjector 1 with the case 2 removed for clarity. FIG. 6E is a related semi-transparent side view of the case 2 with the collar 16. FIGS. 6F and 6G are related longitudinal sections of the autoinjector 1.

When the syringe carrier 8 abuts a front stop (not illustrated) on the case 2, the shroud boss 18 disengages the longitudinal third surface 17.3 and abuts the transversal fourth surface 14. The force of the control spring 9 causes the collar 16 to translate axially and ride along the angled third surface 19.3. Because the shroud boss 18 does not abut the longitudinal third surface, the collar 16 rotates relative to the case 2 in the second rotational direction R2 to a fourth angular position relative to the case 2 due to the angled third surface 19.3. After sufficient rotation of the collar 16 in the second rotational direction R2, the carrier boss 20 disengages the angled third surface 19.3, and the shroud boss 18 moves from contact with the transversal fourth surface 17.4 to the angled fifth surface 17.5 (cf. FIG. 2G). After further rotation of the collar 16 in the second rotational direction R2, the carrier boss 20 abuts the longitudinal fourth surface 19.4, preventing further rotation of the collar 16 in the second rotational direction R2 but allowing for axial translation of the collar 16. The shroud boss 18 applies an axial force on the angled fifth surface 17.5 to push the needle shroud 7 in the distal direction D relative to the case 2. When the carrier boss 20 disengages the longitudinal fourth surface 19.4, the force of the control spring 9 causes the collar 16 to rotate in the second rotational direction R2, because the shroud boss 18 abuts the angled fifth surface 17.5 of the shroud slot 17.

Figure 2H:
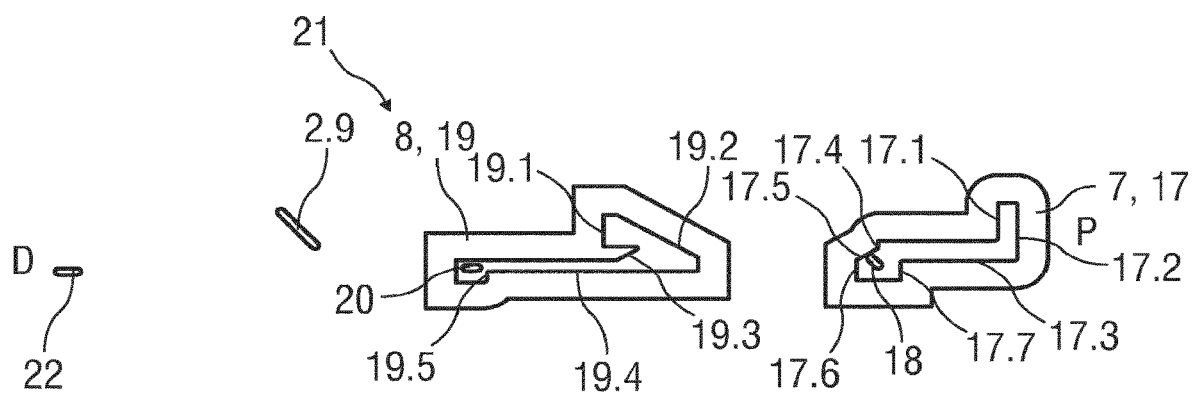
Figure 2I:
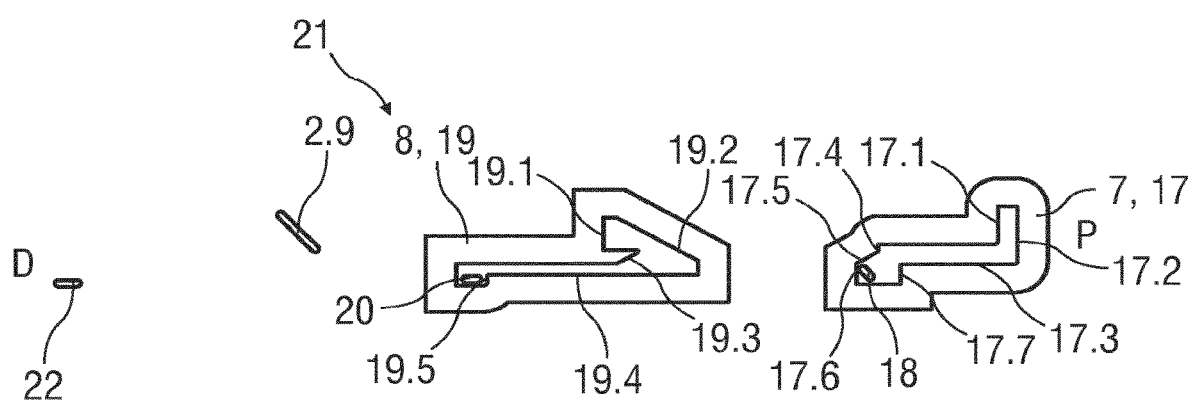

The collar 16 rotates as the shroud boss 18 moves along the angled fifth surface 17.5 from the position shown in FIG. 2H until it abuts the transversal sixth surface 17.6, and the rotation results in the carrier boss 20 engaging a notch adjacent a transversal fifth surface 19.5 in the carrier slot 19 (cf. FIG. 2I). At this point, the needle shroud 7 may abut a front stop (not illustrated) in the case 2. The needle shroud 7 is now in a second extended position SEP extending further from the case 2 in the distal direction D than in the extended position EP thus hiding the extended needle 4. If the needle shroud 7 is attempted to move proximally from the second extended position SEP, the collar 16 is substantially prevented from moving axially relative to the case 2, which prevents the needle shroud 7 from moving proximally relative to the case 2 from the second extended position SEP. The syringe carrier 8 has locked in an axial position relative to the case 2 (see FIG. 5F in which the first boss 8.4 proximally abuts the narrow section 2.4 of the case 2), and the collar 16 is substantially axially locked relative to the syringe carrier 8 via the engagement of the carrier boss 20 in the notch. If the needle shroud 7 is depressed, the shroud boss 18 will abut the sixth transversal surface 17.6 and prevent the needle shroud 7 from retracting. Thus, the needle shroud 7 is prevented from being retracted and is locked in the second extended position SEP to cover the needle 4. This action is activated as soon as the needle 4 reaches insertion depth, and hence the needle 4 will always be shrouded upon removal from the injection site. This reduces the risk of needle stick injury.

Figure 7A:
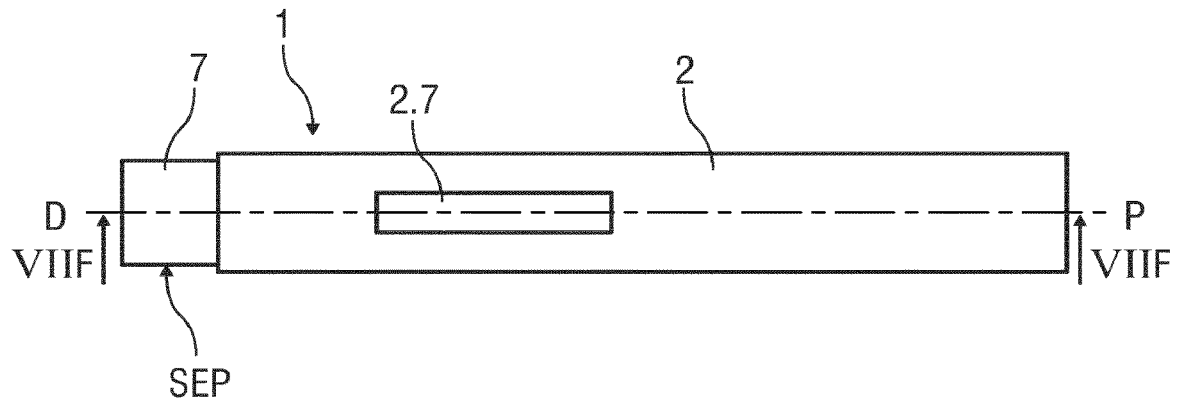
FIG. 7A is a side view of an exemplary embodiment of an autoinjector according to the present invention after use.
Figure 7B:
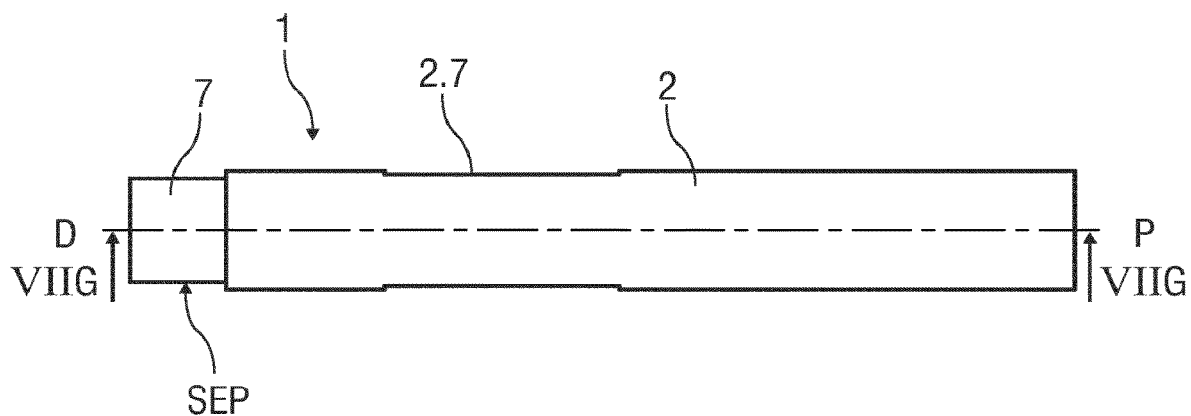
FIG. 7B is a side view of an exemplary embodiment of an autoinjector according to the present invention after use.
Figure 7C:
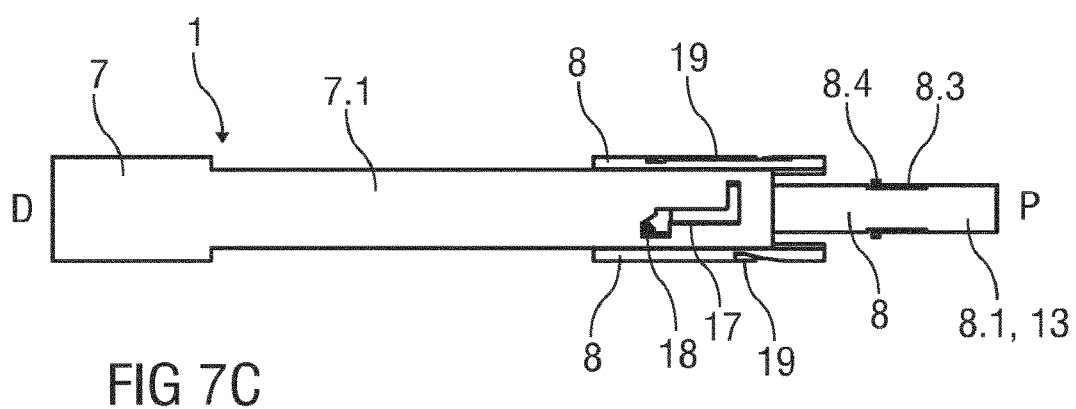
FIG. 7C is a side view of an exemplary embodiment of an autoinjector according to the present invention after use.
Figure 7D:
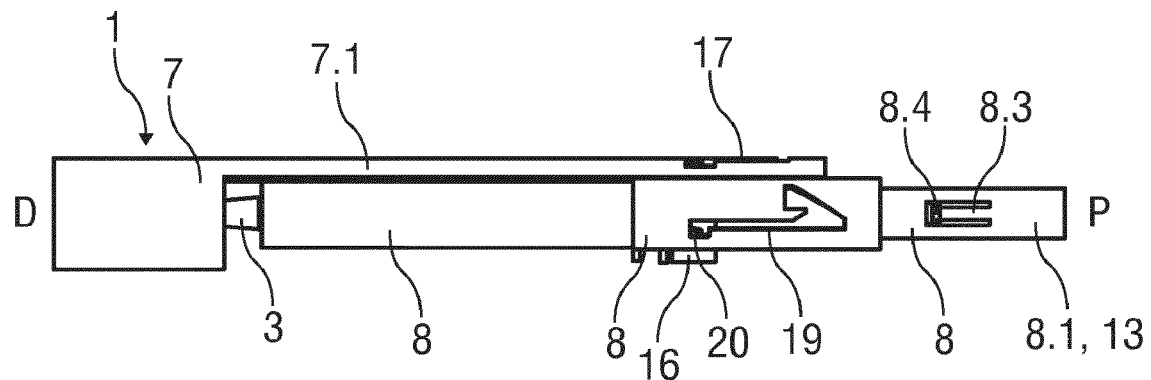
FIG. 7D is a side view of an exemplary embodiment of an autoinjector according to the present invention after use.
Figure 7E:
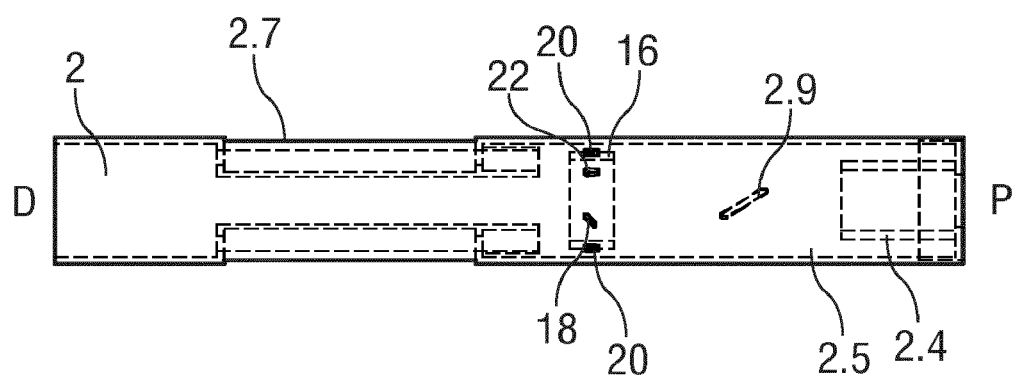
FIG. 7E is a semi-transparent side view of an exemplary embodiment of an autoinjector according to the present invention after use.
Figure 7F:
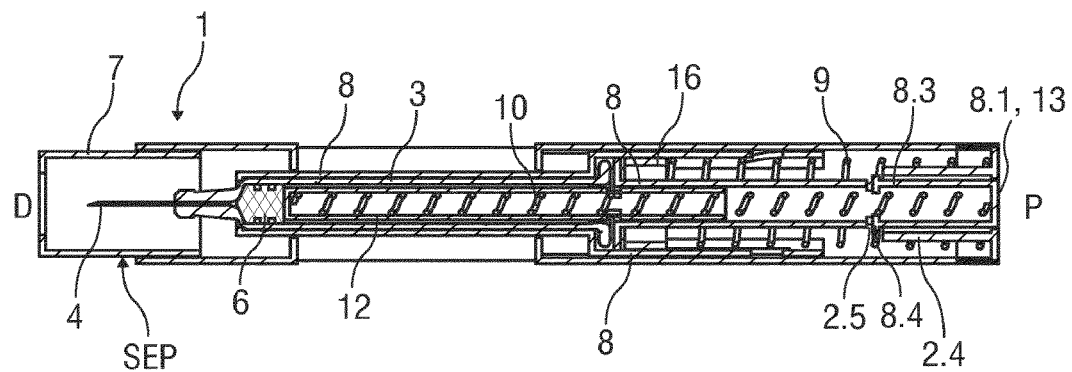
FIG. 7F is a longitudinal section of an exemplary embodiment of an autoinjector according to the present invention after use.
Figure 7G:
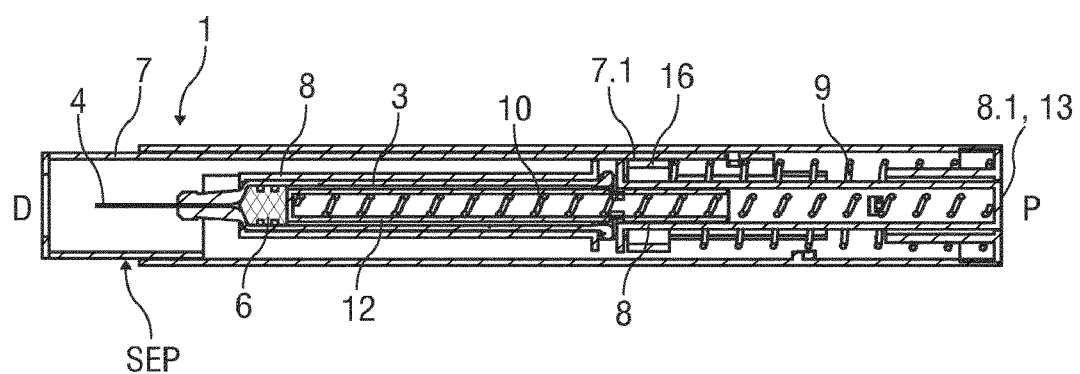
FIG. 7G is a longitudinal section of an exemplary embodiment of an autoinjector according to the present invention after use.

FIGS. 7A and 7B are different side views of an exemplary embodiment of the autoinjector 1 removed from the injection site with the needle shroud 7 in the second extended position SEP. FIGS. 7C and 7D are related side views of the autoinjector 1 with the case 2 removed for clarity. FIG. 7E is a related semi-transparent side view of the case 2 with the collar 16. FIGS. 7F and 7G are related longitudinal sections of the autoinjector 1.

In an exemplary embodiment, the shroud boss 18 could be arranged on the needle shroud 7 and engaged in the shroud slot 17, which would be arranged in the collar 16. Likewise the carrier boss 20 could be arranged on the syringe carrier 8 and engaged in the carrier slot 19, which would be arranged in the collar 16. Likewise the angled case rib 2.9 could be arranged on the collar 16 and the case boss 22 on the case 2.

In another exemplary embodiment, the control mechanism 21 could be adapted to be applied in an autoinjector 1 without the trigger button 13, but which is activated based on depression of the needle shroud 7. For example, the a modified control mechanism 21 could include, e.g. a steeper angle of the angled second surface 19.2 of the carrier slot 19, a reduced length of the transversal first surface 17.1 of the shroud slot 17, and/or a reduced length of the angled case rib 2.9.

In an exemplary embodiment, the case 2 may comprise a front case and a rear case which are attached to form the case 2, in order to facilitate assembly.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein praline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37Exendin-4(1-39)-NH2,
H-(Lys)5-des Pro36, des Pro37Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39), des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two 13 sheets create a "sandwich" shape, held together by interactions between conserved cysteines and other charged amino acids.

There are five types of mammalian Ig heavy chain denoted by a, o, £, y, and μ. The type of heavy chain present defines the isotype of antibody; these chains are found in IgA, IgD, IgE, IgG, and IgM antibodies, respectively.

Distinct heavy chains differ in size and composition; a and y contain approximately 450 amino acids and O approximately 500 amino acids, while μ and £ have approximately 550 amino acids. Each heavy chain has two regions, the constant region (CH) and the variable region (VH)— In one species, the constant region is essentially identical in all antibodies of the same isotype, but differs in antibodies of different isotypes. Heavy chains y, a and o have a constant region composed of three tandem Ig domains, and a hinge region for added flexibility; heavy chains μ and £ have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by 'A and K. A light chain has two successive domains: one constant domain (CL) and one variable domain (VL). The approximate length of a light chain is 211 to 217 amino acids. Each antibody contains two light chains that are always identical; only one type of light chain, K or 'A, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-06-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. An autoinjector comprising:
   a case having a rib;
   a needle shroud telescopically coupled to the case and movable between a first extended position, a retracted position and a locked second extended position;
   a carrier arranged in the case and adapted to hold a medicament container,
   a plunger slidably coupled to the carrier;
   a drive spring biasing the plunger relative to the carrier, the plunger movable from a first axial position to a second axial position relative to the case; and
   a collar slidably disposed in the case, the collar coupled to the needle shroud,
   wherein the plunger abuts the rib when the needle shroud is in the first extended position, and the plunger disengages the rib when the needle shroud is in the retracted position.

2. The autoinjector according to claim 1 wherein the collar includes a shroud boss adapted to engage a plunger boss on the plunger and a case boss adapted to engage the rib of the case.

3. The autoinjector according to claim 2, wherein the shroud boss, a carrier boss and the case boss are disposed in approximately a same plane on the collar.

4. The autoinjector according to claim 1, wherein the carrier includes a compliant beam having a boss adapted to engage an opening in the plunger when the carrier is in a first axial position.

5. The autoinjector according to claim 4, wherein the boss is adapted to engage the case when the carrier is in a second axial position.

6. The autoinjector according to claim 1, wherein the collar is in a first angular position relative to the case when the needle shroud is in the first extended position and the carrier is in the first axial position.

7. The autoinjector according to claim 6, wherein the collar rotates to a second angular position relative to the case and translates proximally relative to the case when the needle shroud moves from the first extended position to the retracted position.

8. The autoinjector according to claim 7, wherein the collar translates distally relative to the case when the needle shroud is in the retracted position and the carrier moves from the first axial position to a second axial position.

9. The autoinjector according to claim 8, wherein when the carrier is in the second axial position, a boss of a compliant beam disengages an opening in the plunger and the plunger translates axially relative to the carrier under a force of the drive spring advancing the carrier from the second axial position to a third axial position relative to the case.

10. The autoinjector according to claim 9, wherein the collar rotates to a third angular position relative to the case and translates with the needle shroud distally relative to the case when the carrier is in the third axial position.

11. The autoinjector according to claim 10, wherein the collar rotates to a fourth angular position relative to the case when the needle shroud is in the locked second extended position.

12. The autoinjector according to claim 11, wherein a shroud boss engages a shroud slot notch in a shroud slot and a carrier boss engages a carrier slot notch in a carrier slot when the collar is in the fourth angular position and the needle shroud is in the locked second extended position.

13. The autoinjector according to claim 12, wherein the engagement of the carrier boss and the carrier slot notch substantially fixes the collar in an axial position relative to the case.

14. The autoinjector according to claim 1, further comprising:
   a control spring biasing the collar relative to the case.

15. The autoinjector according to claim 1, further comprising:
   a trigger button coupled to or integral with the carrier.

* * * * *